United States Patent
Cabuz et al.

(10) Patent No.: US 7,420,659 B1
(45) Date of Patent: Sep. 2, 2008

(54) FLOW CONTROL SYSTEM OF A CARTRIDGE

(75) Inventors: Cleopatra Cabuz, Eden Prairie, MN (US); Eugen Cabuz, Eden Prairie, MN (US)

(73) Assignee: Honeywell Interantional Inc., Morristown, NJ (US)

( * ) Notice: Subject to any disclaimer, the term of this patent is extended or adjusted under 35 U.S.C. 154(b) by 308 days.

(21) Appl. No.: 10/908,014

(22) Filed: Apr. 25, 2005

Related U.S. Application Data

(60) Continuation-in-part of application No. 10/980,685, filed on Nov. 3, 2004, now Pat. No. 6,968,862, and a continuation-in-part of application No. 10/340,231, filed on Jan. 10, 2003, now Pat. No. 6,889,567, and a continuation-in-part of application No. 10/304,773, filed on Nov. 26, 2002, and a division of application No. 10/174,851, filed on Jun. 19, 2002, now Pat. No. 6,837,476, and a continuation-in-part of application No. 09/630,924, filed on Aug. 2, 2000, now Pat. No. 6,597,438, and a division of application No. 09/586,093, filed on Jun. 2, 2000, now Pat. No. 6,568,286.

(51) Int. Cl.
*G01N 33/49* (2006.01)
*F04B 17/00* (2006.01)

(52) U.S. Cl. .................. 356/39; 417/413.1; 417/322

(58) Field of Classification Search .................. None
See application file for complete search history.

(56) References Cited

U.S. PATENT DOCUMENTS 2,403,692 A 7/1946 Tibetts
2,975,307 A 3/1961 Shroeder et al.
3,304,446 A 2/1967 Martinek et al.
3,381,623 A 5/1968 Elliot
3,414,010 A 12/1968 Sparrow
3,641,373 A 2/1972 Elkuch
3,769,531 A 10/1973 Elkuch
3,803,424 A 4/1974 Smiley et al.

(Continued)

FOREIGN PATENT DOCUMENTS

CN 677136 4/1991

(Continued)

OTHER PUBLICATIONS http://www.micronics.net/tsensor.htm, 2 pages, downloaded Jun. 14, 2000.

(Continued)

*Primary Examiner*—Gregory J. Toatley, Jr.
*Assistant Examiner*—Juan D Valentin
(74) *Attorney, Agent, or Firm*—Kris T. Fredrick

(57) ABSTRACT

An apparatus having a disposable cytometer cartridge containing pumps, pressure chambers, reservoirs, flow sensors, flow channels, and microfluidic circuits with fluid operations on the cartridge. The circuits may include mesopumps and mesovalves embedded in the chip, card or cartridge. The apparatus may have multiple detecting, analyzing and identification capabilities of blood or other fluids of interest. The sample to be tested may be entered in the disposable microfluidic cartridge which in turn is insertable in a hand-holdable or portable cytometer instrument. This apparatus may have significant application in biological warfare agent detection, water analyses, environmental checks, hematology, and other clinical and research fields.

24 Claims, 30 Drawing Sheets

U.S. PATENT DOCUMENTS

| | | |
|---|---|---|
| 3,822,095 A | 7/1974 | Hirschfeld |
| 3,928,094 A | 12/1975 | Angell |
| 3,947,644 A | 3/1976 | Uchikawa |
| 3,976,862 A | 8/1976 | Curbelo |
| 3,993,939 A | 11/1976 | Slavin |
| 4,115,036 A | 9/1978 | Paterson |
| 4,140,936 A | 2/1979 | Bullock |
| 4,197,737 A | 4/1980 | Pittman |
| 4,284,412 A | 8/1981 | Hansen et al. |
| 4,360,955 A | 11/1982 | Block |
| 4,418,886 A | 12/1983 | Holzer |
| 4,453,169 A | 6/1984 | Martner |
| 4,478,076 A | 10/1984 | Bohrer |
| 4,478,077 A | 10/1984 | Boher |
| 4,498,850 A | 2/1985 | Perlov et al. |
| 4,501,144 A | 2/1985 | Higashi et al. |
| 4,539,575 A | 9/1985 | Nilsson |
| 4,576,050 A | 3/1986 | Lambert |
| 4,581,624 A | 4/1986 | O'Connor |
| 4,585,209 A | 4/1986 | Aine et al. |
| 4,599,000 A | 7/1986 | Yamada |
| 4,619,438 A | 10/1986 | Coffee |
| 4,651,564 A | 3/1987 | Johnson et al. |
| 4,654,546 A | 3/1987 | Kirjavainen |
| 4,683,159 A | 7/1987 | Bohrer et al. |
| 4,695,034 A | 9/1987 | Shimizu et al. |
| 4,704,033 A | 11/1987 | Fay et al. |
| 4,722,360 A | 2/1988 | Odajima et al. |
| 4,745,279 A | 5/1988 | Karkar et al. |
| 4,756,508 A | 7/1988 | Giachino et al. |
| 4,818,263 A | 4/1989 | Mitch |
| 4,821,999 A | 4/1989 | Ohtaka |
| 4,829,826 A | 5/1989 | Valentin et al. |
| 4,874,949 A | 10/1989 | Harris et al. |
| 4,898,200 A | 2/1990 | Odajima et al. |
| 4,911,616 A | 3/1990 | Laumann, Jr. |
| 4,932,989 A | 6/1990 | Presby |
| 4,938,742 A | 7/1990 | Smits |
| 4,939,405 A | 7/1990 | Okuyama et al. |
| 5,017,497 A | 5/1991 | de Grooth et al. |
| 5,050,429 A | 9/1991 | Nishimoto et al. |
| 5,065,978 A | 11/1991 | Albarda et al. |
| 5,069,419 A | 12/1991 | Jerman |
| 5,078,581 A | 1/1992 | Blum et al. |
| 5,082,242 A | 1/1992 | Bonne et al. |
| 5,085,562 A | 2/1992 | van Lintel |
| 5,096,388 A | 3/1992 | Weinberg |
| 5,108,623 A | 4/1992 | Cangelosi et al. |
| 5,129,794 A | 7/1992 | Beatty |
| 5,148,074 A | 9/1992 | Fujita et al. |
| 5,171,132 A | 12/1992 | Miyazaki et al. |
| 5,176,358 A | 1/1993 | Bonne et al. |
| 5,180,288 A | 1/1993 | Richter et al. |
| 5,180,623 A | 1/1993 | Ohnstein |
| 5,185,641 A | 2/1993 | Igushi et al. |
| 5,186,054 A | 2/1993 | Sekimura |
| 5,192,197 A | 3/1993 | Culp |
| 5,194,909 A | 3/1993 | Tycko |
| 5,206,557 A | 4/1993 | Bobbio |
| 5,219,278 A | 6/1993 | van Lintel |
| 5,224,843 A | 7/1993 | van Lintel |
| 5,244,527 A | 9/1993 | Aoyagi |
| 5,244,537 A | 9/1993 | Ohnstein |
| 5,322,258 A | 6/1994 | Bosch et al. |
| 5,323,999 A | 6/1994 | Bonne et al. |
| 5,325,880 A | 7/1994 | Johnson et al. |
| 5,336,062 A | 8/1994 | Richter |
| 5,368,571 A | 11/1994 | Horres, Jr. |
| 5,441,597 A | 8/1995 | Bonne et al. |
| 5,452,878 A | 9/1995 | Gravesen et al. |
| 5,457,526 A | 10/1995 | Kosaka |
| 5,499,909 A | 3/1996 | Yamada et al. |
| 5,510,267 A | 4/1996 | Marshall |
| 5,526,172 A | 6/1996 | Kanack |
| 5,528,045 A | 6/1996 | Hoffman et al. |
| 5,529,465 A | 6/1996 | Zengerie et al. |
| 5,536,963 A | 7/1996 | Polla |
| 5,541,465 A | 7/1996 | Higuchi et al. |
| 5,552,654 A | 9/1996 | Konno et al. |
| 5,570,193 A | 10/1996 | Landa et al. |
| 5,571,401 A | 11/1996 | Lewis et al. |
| 5,601,080 A | 2/1997 | Oppenheimer |
| 5,616,501 A | 4/1997 | Rodriguez et al. |
| 5,633,724 A | 5/1997 | King et al. |
| 5,642,015 A | 6/1997 | Whitehead et al. |
| 5,683,159 A | 11/1997 | Johnson |
| 5,696,662 A | 12/1997 | Bauhahn |
| 5,716,852 A | 2/1998 | Yager et al. |
| 5,717,631 A | 2/1998 | Carley et al. |
| 5,725,363 A | 3/1998 | Bustgens et al. |
| 5,726,751 A | 3/1998 | Altendorf et al. |
| 5,747,808 A * | 5/1998 | Wong .................. 356/437 |
| 5,757,476 A | 5/1998 | Nakamoto et al. |
| 5,759,014 A | 6/1998 | Van Lintel |
| 5,759,015 A * | 6/1998 | Van Lintel et al. .......... 417/322 |
| 5,760,900 A | 6/1998 | Ito et al. |
| 5,792,957 A | 8/1998 | Luder et al. |
| 5,793,485 A | 8/1998 | Gourley |
| 5,799,030 A | 8/1998 | Brenner |
| 5,822,170 A | 10/1998 | Cabuz et al. |
| 5,836,750 A | 11/1998 | Cabuz |
| 5,839,467 A | 11/1998 | Saaski et al. |
| 5,839,807 A | 11/1998 | Perlo |
| 5,863,502 A | 1/1999 | Southgate et al. |
| 5,863,708 A * | 1/1999 | Zanzucchi et al. .......... 430/320 |
| 5,880,474 A | 3/1999 | Norton et al. |
| 5,893,722 A | 4/1999 | Hibbs-Brenner et al. |
| 5,901,939 A | 5/1999 | Cabuz et al. |
| 5,911,872 A | 6/1999 | Lewis et al. |
| 5,922,210 A | 7/1999 | Brody et al. |
| 5,932,100 A | 8/1999 | Yager et al. |
| 5,948,684 A | 9/1999 | Weigl et al. |
| 5,954,079 A | 9/1999 | Barth et al. |
| 5,970,315 A | 10/1999 | Carley et al. |
| 5,971,158 A | 10/1999 | Yager et al. |
| 5,971,355 A | 10/1999 | Biegelsen et al. |
| 5,972,710 A | 10/1999 | Weigl et al. |
| 5,974,867 A | 11/1999 | Forster et al. |
| 6,007,775 A | 12/1999 | Yager |
| 6,032,689 A | 3/2000 | Tsai et al. |
| 6,054,335 A | 4/2000 | Sun et al. |
| 6,082,185 A | 7/2000 | Saaski |
| 6,091,197 A | 7/2000 | Sun et al. |
| 6,091,537 A | 7/2000 | Sun et al. |
| 6,094,293 A | 7/2000 | Yokoyama et al. |
| 6,097,485 A | 8/2000 | Lievan |
| 6,097,859 A | 8/2000 | Solgaard et al. |
| 6,106,245 A | 8/2000 | Cabuz |
| 6,109,889 A | 8/2000 | Zengerie et al. |
| 6,116,756 A | 9/2000 | Peeters et al. |
| 6,116,863 A | 9/2000 | Ahn et al. |
| 6,122,973 A | 9/2000 | Nomura et al. |
| 6,124,663 A | 9/2000 | Haake et al. |
| 6,139,800 A | 10/2000 | Chandler |
| 6,151,967 A | 11/2000 | McIntosh et al. |
| 6,167,761 B1 | 1/2001 | Hanzawa et al. |
| 6,179,586 B1 | 1/2001 | Herb et al. |
| 6,182,941 B1 | 2/2001 | Scheurenbrand et al. |
| 6,184,607 B1 | 2/2001 | Cabuz et al. |
| 6,184,608 B1 | 2/2001 | Cabuz et al. |
| 6,211,580 B1 | 4/2001 | Cabuz et al. |
| 6,213,151 B1 * | 4/2001 | Jacobson et al. ............ 137/827 |
| 6,215,221 B1 | 4/2001 | Cabuz et al. |
| 6,237,619 B1 | 5/2001 | Maillefer et al. |

| | | | |
|---|---|---|---|
| 6,240,944 | B1 | 6/2001 | Ohnstein et al. |
| 6,249,341 | B1 | 6/2001 | Basiji et al. |
| 6,255,758 | B1 | 7/2001 | Cabuz et al. |
| 6,281,975 | B1 | 8/2001 | Munk |
| 6,288,472 | B1 | 9/2001 | Cabuz et al. |
| 6,338,820 | B1 * | 1/2002 | Hubbard et al. ............... 422/64 |
| 6,358,021 | B1 | 3/2002 | Cabuz |
| 6,373,682 | B1 | 4/2002 | Goodwin-Johansson |
| 6,382,228 | B1 | 5/2002 | Cabuz et al. |
| 6,418,793 | B1 | 7/2002 | Pechoux et al. |
| 6,432,721 | B1 | 8/2002 | Zook et al. |
| 6,445,053 | B1 | 9/2002 | Cho |
| 6,496,348 | B2 | 12/2002 | McIntosh |
| 6,508,528 | B2 | 1/2003 | Fujii et al. |
| 6,520,753 | B1 | 2/2003 | Grosjean et al. |
| 6,521,188 | B1 * | 2/2003 | Webster ...................... 422/100 |
| 6,537,501 | B1 | 3/2003 | Holl et al. |
| 6,549,275 | B1 | 4/2003 | Cabuz et al. |
| 6,568,286 | B1 | 5/2003 | Cabuz |
| 6,572,830 | B1 * | 6/2003 | Burdon et al. ......... 422/186.29 |
| 6,590,267 | B1 | 7/2003 | Goodwin-Johansson et al. |
| 6,597,438 | B1 | 7/2003 | Cabuz et al. |
| 6,640,642 | B1 | 11/2003 | Onose et al. |
| 6,644,117 | B1 | 11/2003 | Kueck et al. |
| 6,649,416 | B1 | 11/2003 | Kauer et al. |
| 6,651,506 | B2 | 11/2003 | Lee et al. |
| 6,700,130 | B2 | 3/2004 | Fritz |
| 6,729,856 | B2 | 5/2004 | Cabuz et al. |
| 6,750,589 | B2 | 6/2004 | Cabuz |
| 6,758,107 | B2 | 7/2004 | Cabuz |
| 6,767,190 | B2 | 7/2004 | Cabuz et al. |
| 6,837,476 | B2 | 1/2005 | Cabuz et al. |
| 7,134,486 | B2 * | 11/2006 | Santiago et al. ........ 165/104.28 |
| 2002/0078756 | A1 | 6/2002 | Akiyama et al. |
| 2002/0174706 | A1 | 11/2002 | Gokhfeld |
| 2002/0192113 | A1 | 12/2002 | Uffenheimer et al. |
| 2003/0005774 | A1 | 1/2003 | Suzuki et al. |
| 2003/0019299 | A1 | 1/2003 | Horie et al. |
| 2003/0033884 | A1 | 2/2003 | Beekhuizen et al. |
| 2003/0142291 | A1 | 7/2003 | Padmanabhan et al. |
| 2003/0189809 | A1 | 10/2003 | Ishikura |
| 2003/0205090 | A1 | 11/2003 | Jakobsen |
| 2003/0234376 | A1 | 12/2003 | Cabuz et al. |
| 2004/0020265 | A1 | 2/2004 | Cabuz |
| 2004/0035211 | A1 | 2/2004 | Pinto et al. |
| 2004/0060360 | A1 | 4/2004 | Chen |

FOREIGN PATENT DOCUMENTS

| | | |
|---|---|---|
| DE | 19617852 | 1/1993 |
| DE | 10122321 | 4/2002 |
| EP | 0269076 | 6/1988 |
| EP | 0744821 A2 | 11/1996 |
| EP | 0744821 A3 | 12/1996 |
| EP | 1001326 | 5/1999 |
| EP | 1134548 | 9/2001 |
| JP | 61066947 | 4/1986 |
| JP | 05-219760 | 8/1993 |
| JP | 02-86258 | 10/1995 |
| JP | 10073528 | 8/1996 |
| JP | 2000056228 | 7/1999 |
| SU | 744877 | 6/1980 |
| WO | WO 95/27199 | 3/1995 |
| WO | WO 97/29538 | 8/1997 |
| WO | WO 99/60397 | 4/1999 |
| WO | 0017624 | 3/2000 |
| WO | WO 00/28215 | 5/2000 |
| WO | WO 01/09598 | 7/2000 |
| WO | 0121962 | 3/2001 |
| WO | WO 01/33078 | 5/2001 |
| WO | WO 02/10713 A2 | 2/2002 |
| WO | WO 02/10713 A3 | 2/2002 |
| WO | WO 02/10714 | 2/2002 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

"Large-Scale Linearization Circuit for Electrostatic Motors" IBM Technical Disclosure Bulletin, U.S. IBM Corporation, vol. 37, No. 10, pp. 563-564, Oct. 1, 1994.

Altendorf et al, "Results Obtained Using A Prototype Microfluidics-Based Hematology Analyzer", SPIE Biomedical Optics 97, 1997.

Altendorf et al., "Differential Blood Cell Counts Obtained Using A Microchannel Based Flow Cytometer", Solid State Sensors & Actuators, vol. 1, 531, 1997.

Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.

Altendorf et al., "Microfabrication Technology For Research And Diagnostics, Silicon Microchannel Optical Flow Cytometry", SPIE Proceedings, Biomedical Optics 96, Jan. 1996.

Athavale et al., "Coupled Electrostatics-Structures-Fluidic Simulations of A Bead Mesopump," Proceedings of the International Mechanical Engineers Congress & Exhibition, Nashville, Tennessee, Oct. 1999.

B. Halg, "On a Nonvolatile Memory Cell Based on Micro-Electro-Mechanics", Proceedings of MEMS CH2832-4/90/0000-0172 IEEE (1990), pp. 172-176.

Bonne et al. "Actuation-Based Fuel Gas Microsensors", IGT Symposium on "Natural Gas Quality, Energy Measurement, Metering and Utilization Practices", Orlando, FL, 17 pages, Mar. 2001.

Branebjerg, Gravesen, "A New Electrostatic Actuator Providing Improved Stroke Length and Force." Micro Elctro Mechanical Systems '92 (Feb. 4-7, 1992), pp. 6-11.

Bustgens, Bacher, Menz, Schomburg, "Micropump Manufactured by Thermoplastic Molding" MEMS 1994, pp. 18-21.

C. Cabuz et al., "Factors Enhancing the Reliability of Touch-Mode Electrostatic Actuators," Sensors and Actuators 79(2000) pp. 245-250.

C. Cabuz et al., "Mesoscopic Sampler Based on 3D Array of Electrostatically Activated Diaphragms," Proceedings of the 10th Int. Conf. On Solid-State Sensors and Actuators, Transducers'99, Jun. 7-12, 1999, Sendai Japan.

C. Cabuz et al., "The Double Diaphragm Pump," The 14th IEEE International Micro Electro Mechanical Systems conference, MEMS'01, Jan. 21-23, Interlachen, Switzerland.

C. Cabuz, et al., "High Reliability Touch-Mode Electrostatic Actuators", Technical Digest of the Solid State Sensor and Actuator Workshop, Hilton Head, S.C., Jun. 8-11, 1998, pp. 296-299.

C. Cabuz. Tradeoffs in MEMS Material (Invited Paper) Proceedings of the SPIE, vol. 2881, pp. 160-170, Austin, TX., Jul. 1996.

Cabuz, Cleopatra, "Electrical Phenomena at the Interface of Rolling-Contact, Electrostatic Actuators", Nanotribology: Critical Assessment and Research Needs, Kluwer Academic Publisher, pp. 221-236, Copyright 2003, presented at the Nanotribology Workshop, Mar. 13-15, 2000.

Cleo Cabuz, "Dielectric Related Effects in Micromachined Electrostatic Actuators," Annual Report of the IEEE/CEIDP Society, 1999, Annual Meeting, Austin, Texas, Oct. 17-20, 1999.

Darling et al., "Integration Of Microelectrodes With Etched Microchannels For In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego California, Feb 11-15, 1996, pp. 13-18.

Hatch et al., "Microfluidic Approaches To Immunoassays", SPIE conference on Micromachining and Microfabrication Symposium at Santa Clara, CA, Sep. 20-22, 1999.

Huang et al., "Development Of A Flow Cytometry Based Miniature Chemical Fluid Analysis System Using Fluorescent Microbeads", SPIE Biomedical Optics, BIOS 97, conference proceedings, 1997.

Jye-Shane Yang et al., "Fluorescent Porous Polymer Films as TNT Chemosensors: Electronic and Structural Effects", *J. Am. Chem. Soc.*, 1998, 120, pp. 11864-11873.

Jye-Shane Yang et al., "Porous Shape Persistent Fluorescent Polymer Films: An Approach to TNT Sensory Materials", *J. Am. Chem. Soc.*, 1998, 120, pp. 5321-5322.

Lehman et al., "High-Frequency Modulation Characteristics of Red VCSELs", Electronics Letters, Feb. 13, 1997, vol. 33(4), pp. 298-300. Copyright 1997 IEE.

Michael S. Freund et al., "Chemically Diverse Conducting Polymer-Based 'Electronic Nose'", Proceedings of the National Academy of Sciences of the United States of America, vol. 92, No. 7, Mar. 28, 1995, pp. 2652-2656.

Minami K et al., "Fabrication of Distributed Electrostatic Micro Actuator (DEMA)" Journal of Microelectromechanical Systems, US, IEEE Inc., New York, vol. 2, No. 3, Sep. 1, 1993, pp. 121-127, XP000426532, ISSN: 1057-7157.

Ohnstein et al., "Micromachined Silicon Microvalve", Micro Electromechanical Systems Workshop, Salt Lake City, UT, 4 pages, Feb. 20-22, 1990.

Porex Technologies, brochure, dated prior to Jun. 2, 2000, 4 pages.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practial Flow Cytometry", third edition, 1995, p. 237.

Shikida, Sato, "Characteristics of an Electrostatically-Driven Gas Valve Under High Pressure Conditions, IEEE 1994, pp. 235-240".

Shikida, Sato, Harada, "Fabrication of An S-Shaped Microactuator," Journal of Microelectromechanical Systems, vol. 6, No. 1 (Mar. 1997), pp. 18-24.

Shikida, Sato, Tanaka, Kawamura, Fujisaki, "Electrostatically Driven Gas Valve With High Conductance", Journal of Microelectromechanical Systems, vol. 3, No. 2 (Jun. 1994), pp. 76-80.

Srinivasan et al., "Self-Assembled Fluorocarbon Films for Enhanced Stiction Reduction", Transducers '97, 1997 International Conference on Solid-State Sensors and Actuators, Chicago, Jun. 16-19, 1997, pp. 1399-1402.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3rd International Conference on Micro Opto Electro Mechanical Systems (MOEMS 99), Aug. 30-Sep. 1, 1999, Mainz, Germany, pp. 165-170.

Toshiyoshi et al., "Surface micromachined 2D Lens Scanner Array", Proc. IEEE?LEOS International Conference on Optical EMMS/ Sheraton Kauai Resort, Kauai, Hawaii, Aug. 21-24, 2000, 2 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array For Beam Steering and Precision Alignment in Optical Interconnect Systems", Solid-State Sensor and Actuator Workshop, Hilton Head Island, South Carolina, Jun. 4-8, 2000, pp. 101-104.

Wagner, Quenzer, Hoerscelmann, Lisec, Juerss, "Bistable Microvalve with Pneumatically Coupled Membranes," 0-7803-2985-6/96, IEEE (1996), pp. 384-388.

Weigh et al, "Silicon-Microfabricated Diffusion-Based Optical Chemical Sensor", Reprint from "Sensors & Actuators" B 38-39, 452-457, 1997.

Weigl et al, "Microfluidic Diffusion-Based Separation And Detection", Science, vol. 283, pp. 346-347, Jan. 15, 1999.

Weigl et al, "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al, "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection In Silicon Flow Structures", B. Weigl et al., Analytical Methods & Instrumentation, µTTAS 96 special edition, 1996.

Weigl et al., "Fluorescence And Absorbance Analyte Sensing In Whole Blood And Plasma Based On Diffusion Separation In Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", µTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Yager et al., "Applying Microfluidic Chemical Analytical Systems To Imperfect Samples", Micro Total Analysis Systems 98, D. Harrison & A. van den Berg (ed.), Kluwer Academic Publishers, Dordrecht, 207-212, 1998.

Yager et al., "Design Of Microfluidic Sample Preconditioning Systems For Detection Of Biological Agents In Environmental Samples", Yager, M. et al., SPIE Proceedings, 3515, 252-259, 1998.

Bertz, et al., Silicon Grooves with Sidewall Angles Down to 1° Made by Dry Etching, Micro System Technologies '94, 4th International Conference on Micro Electro, Opto, Mechanical Systems and Components, Berlin, Oct. 19-21, 1994, pp. 331-339.

Sia et al., "Microfluidic devices fabricated in poly(dimethylsilozane) for biological studies,"Electrophoresis 2003, 24, pp. 3563-3576, Jun. 19, 2003.

\* cited by examiner

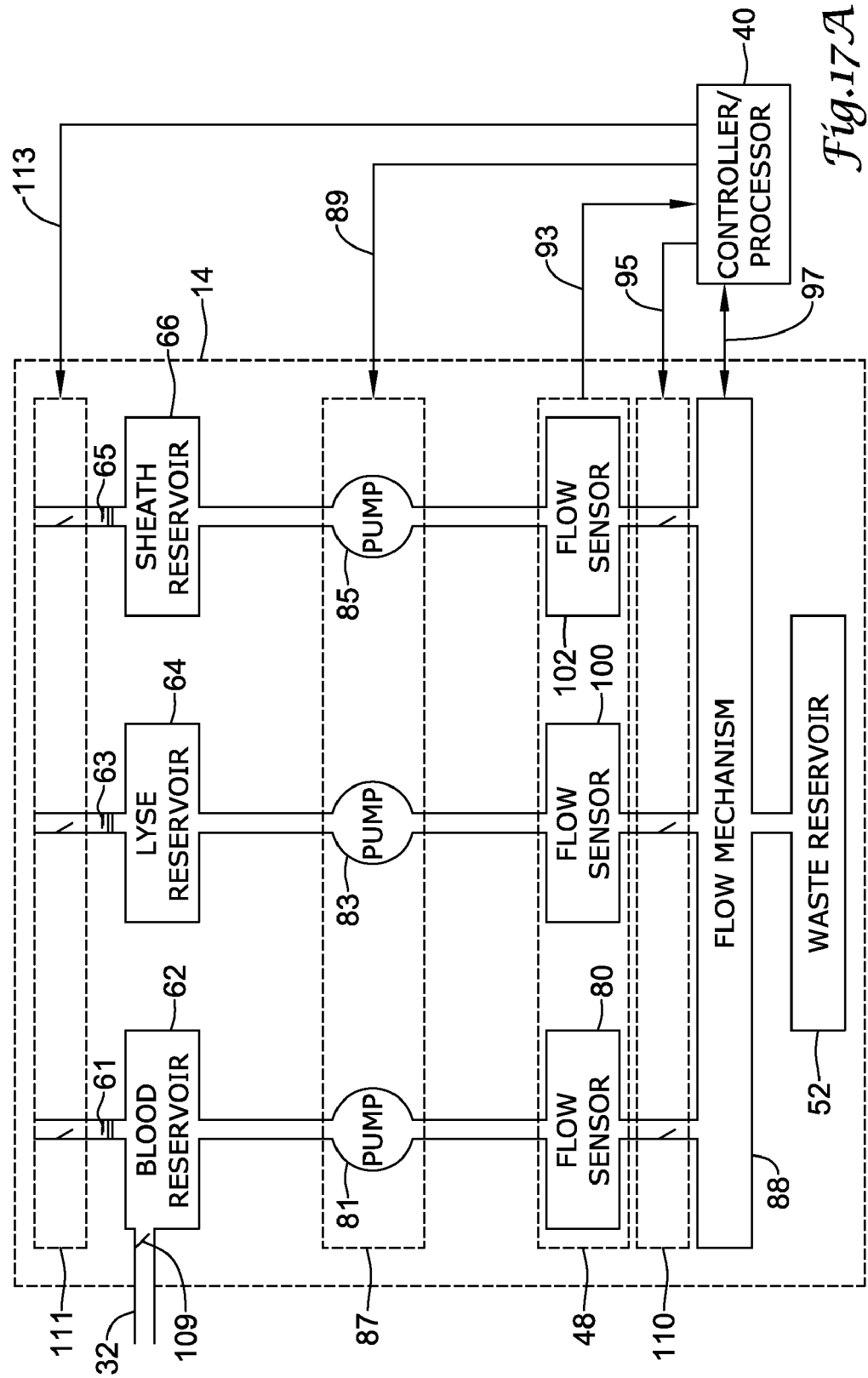

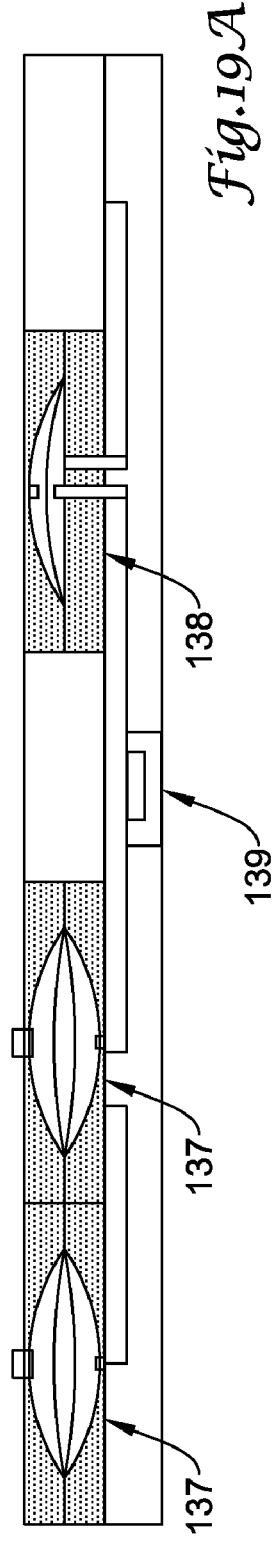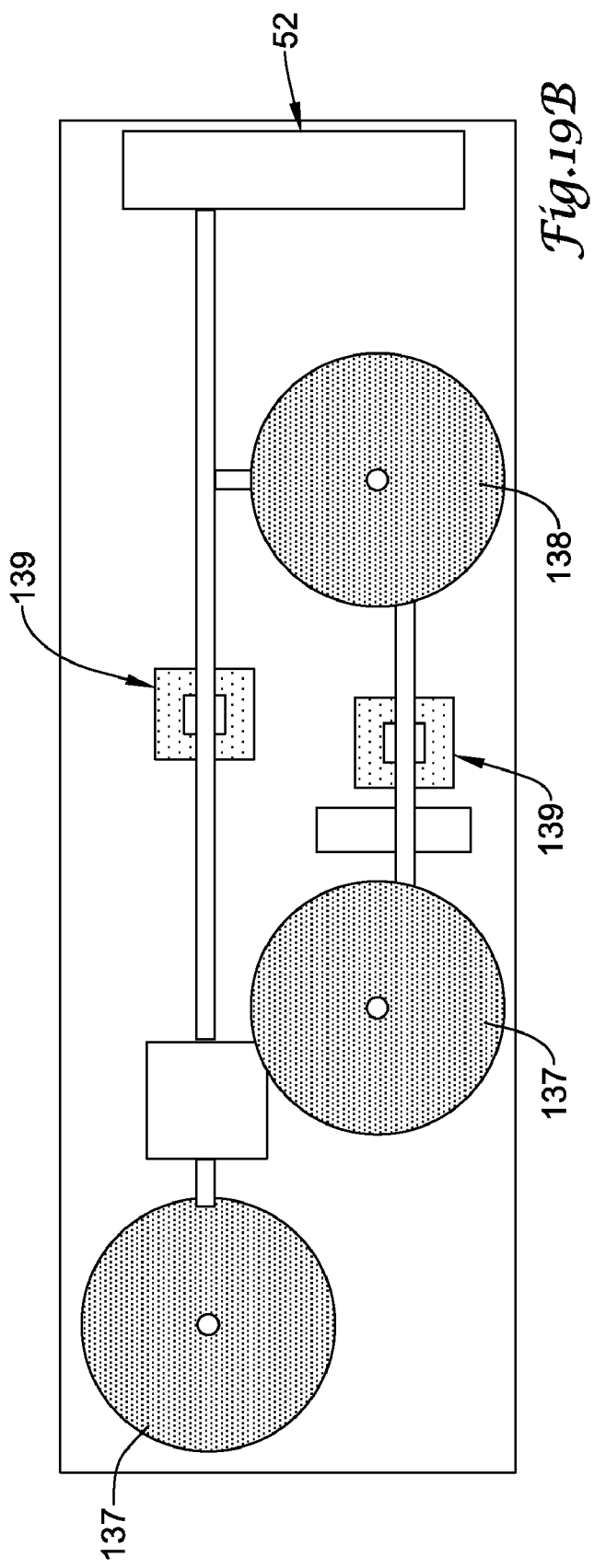
Fig. 19A
Fig. 19B

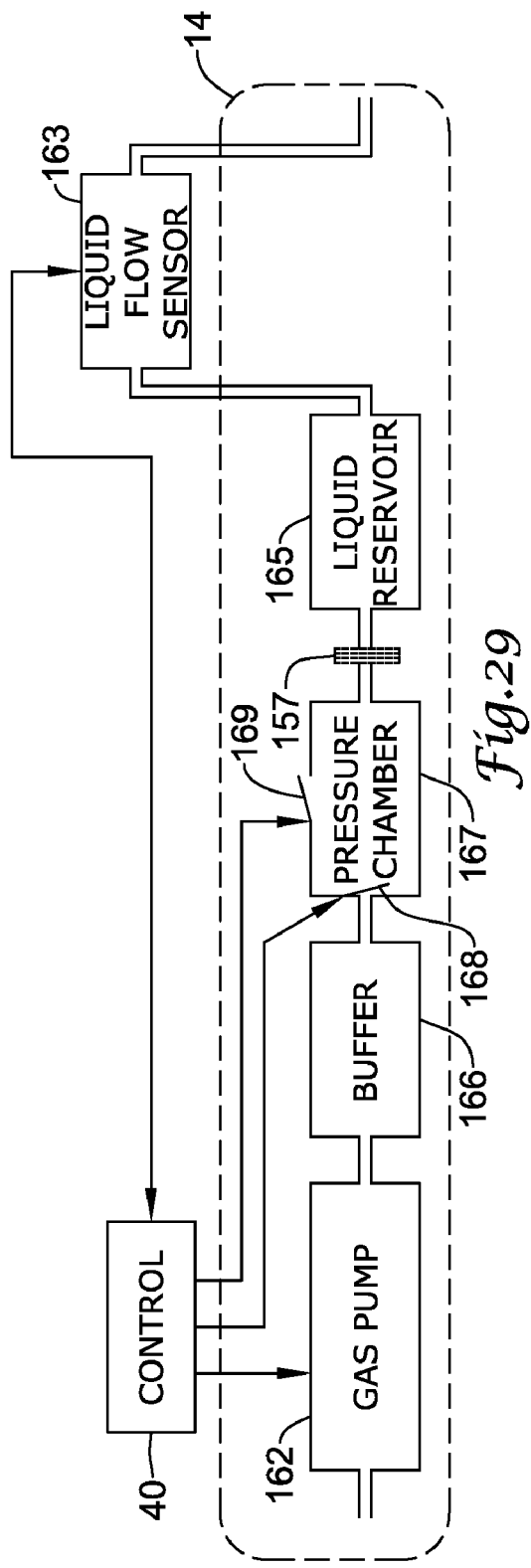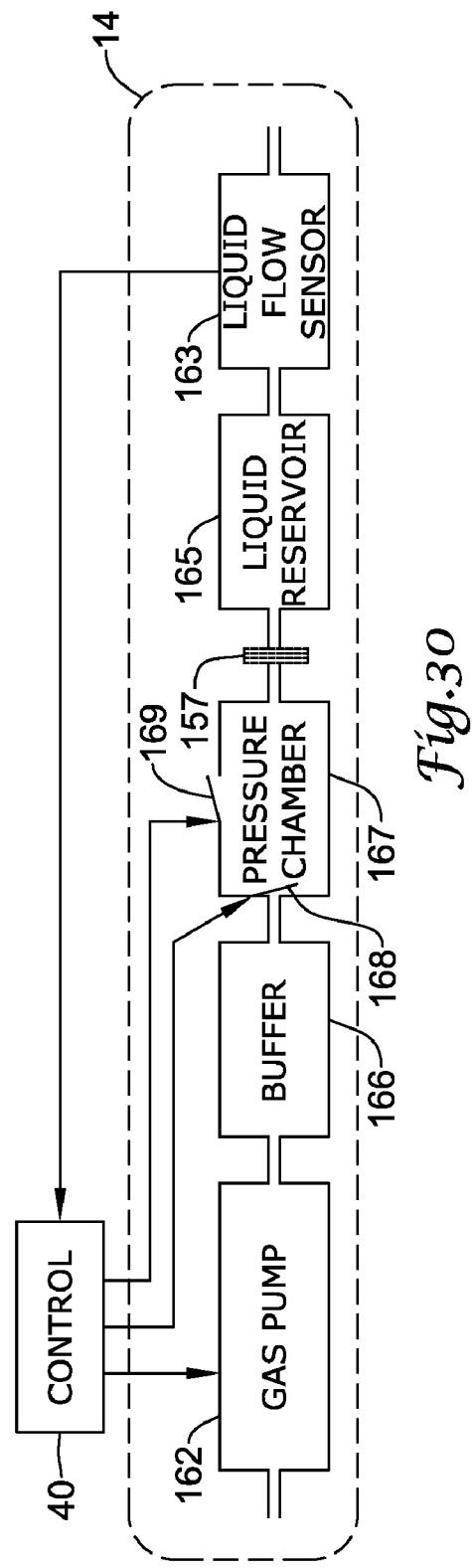

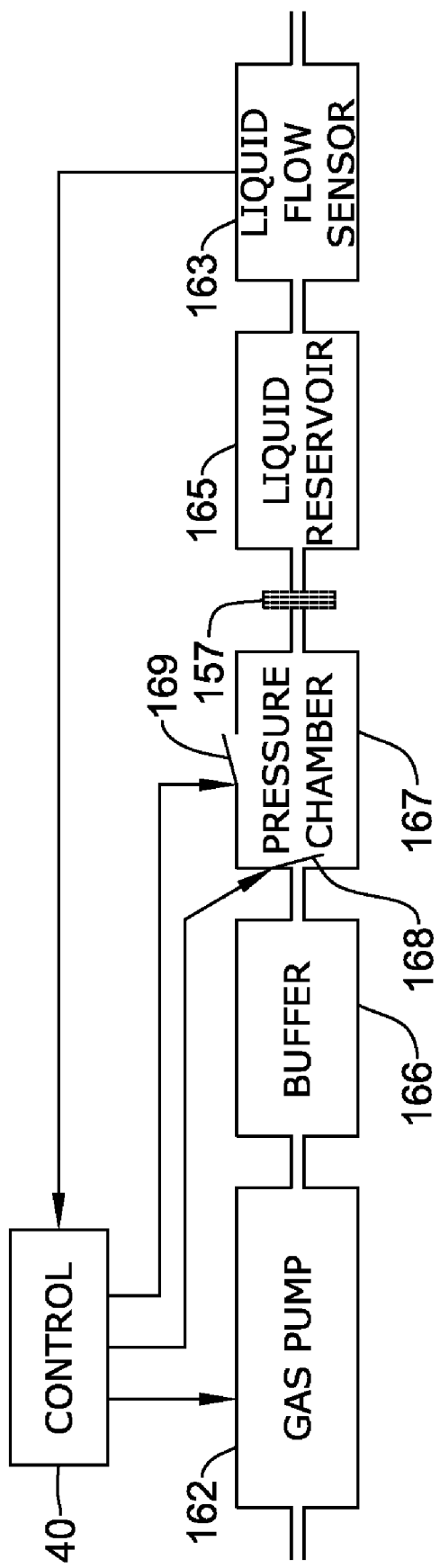

FLOW CONTROL SYSTEM OF A CARTRIDGE

This present application is a continuation-in-part of U.S. patent application Ser. No, 10/304,773, filed Nov. 26, 2002, which is a continuation-in-part of U.S. patent application Ser. No. 09/630,924, filed Aug. 2, 2000, now U.S. Pat. No. 6,597,438 B1, and claims the benefit thereof. Also, this present application is a continuation-in-part of U.S. patent application Ser. No. 10/980,685, filed Nov. 3, 2004, which is a division of U.S. patent application Ser. No. 10/174,851, filed Jun. 19, 2002, now U.S. Pat. No. 6,837,476, and claims the benefit thereof. Also, this present application is a continuation-in-part of U.S. patent application Ser. No. 10/340,231, filed Jan. 10, 2003, which is a division of U.S. patent application Ser. No. 09/586,093, filed Jun. 2, 2000, now U.S. Pat. No. 6,568,286 B1, and claims the benefit thereof. All of the above-mentioned patent documents are incorporated herein by reference.

GOVERNMENT SUPPORT

This invention was made with government support under DARPA contract number MDA972-00-C-0029. The government may have certain rights in the invention.

The present invention is related to U.S. patent application Ser. No. 10/905,995, filed Jan. 28, 2005, by Cabuz et al., entitled "Mesovalve Modulator", and incorporated herein by reference. Also, the present invention is related U.S. patent application Ser. No. 11/018,799, filed Dec. 21, 2004, by Cabuz et al., entitled "Media Isolated Electrostatically Actuated Valve", and incorporated herein by reference. These applications are owned by the same entity that owns the present invention.

The present invention is also related to U.S. Pat. No. 6,549,275 B1, issued Apr. 15, 2003 to Cabuz et al., and entitled "Optical Detection System for Flow Cytometry"; U.S. Pat. No. 6,382,228 B1, issued May 7, 2002 to Cabuz et al., and entitled "Fluid Driving System for Flow Cytometry"; U.S. Pat. No. 6,700,130 B2, issued Mar. 2, 2004 to Fritz, and entitled "Optical Detection System for Flow Cytometry"; U.S. Pat. No. 6,729,856 B2, issued May 4, 2004, to Cabuz et al., and entitled "Electrostatically Actuated Pump with Elastic Restoring Forces"; U.S. Pat. No. 6,255,758 B1, issued Jul. 3, 2001, to Cabuz et al., and entitled "Polymer Microactuator Array with Macroscopic Force and Displacement"; U.S. Pat. No. 6,240,944 B1, issued Jun. 5, 2001 to Ohnstein et al., and entitled "Addressable Valve Arrays for Proportional Pressure or Flow Control"; U.S. Pat. No. 6,179,586 B1, issued Jan. 30, 2001 to Herb et al., and entitled "Dual Diaphragm, Single Chamber Mesopump"; and U.S. Pat. No. 5,836,750, issued Nov. 17, 1998 to Cabuz, and entitled "Electrostatically Actuated Mesopump Having a Plurality of Elementary Cells"; all of which are incorporated herein by reference. These patents are owned by the same entity that owns the present invention.

BACKGROUND

The present invention relates generally to flow cytometers. More particularly, the present invention relates to portable flow cytometers that sense optical properties of microscopic biological particles or components in a flow stream.

Flow cytometry is a technique that is used to determine certain physical and chemical properties of microscopic biological particles or components by sensing certain optical properties of the particles or components. To do so, for instance, the particles may be arranged in single file using hydrodynamic focusing within a sheath fluid. The particles are then individually interrogated by a light beam. Each particle scatters the light beam and produces a scatter profile. The scatter profile is often identified by measuring the light intensity at different scatter angles. Certain physical and/or chemical properties of each particle can then be determined from the scatter profile.

Flow cytometry is currently used in a wide variety of applications including hematology, immunology, genetics, food science, pharmacology, microbiology, parasitology, oncology, biological agent detection, and environmental science, to name a few. A limitation of many commercially available flow cytometer systems is that they are relatively large bench top instruments that must remain in a central laboratory environment. Accordingly, the use of such flow cytometers is often not available in remote locations or for continuous hematological monitoring.

SUMMARY

The present invention can overcome many of the disadvantages of the related art by providing a highly miniaturized portable and wearable apparatus (e.g., cytometer) that is usable at remote locations, such as at home or in the field. The apparatus may incorporate fluid devices and operations on a disposable cartridge, chip or card, with optical and electrical interfaces external to the cartridge. Such an apparatus may help improve healthcare of patients by providing detailed individual hematological evaluation and uncovering statistical trends. By detecting an infection early, the infection may be more readily treatable. The apparatus may also be used in non-medical applications such as those in various environmental and industrial areas.

In military applications, the apparatus may be a portable miniaturized cytometer of the present invention may help save lives by providing early detection of infection due to biological agents. It is known that expanded activity in the biological sciences has increased the probability of accidental exposure to dangerous biological agents. The ease of manufacturing such agents also raises a serious threat to their use by terrorists, regional powers or developing third world nations. The lack of safeguards in international agreements outlawing biological warfare, and compelling evidence that those agreements may have been violated, reinforces the need for a strong capability for biological defense. Pre-exposure detection of pathogen agents, as well as post-exposure detection of incipient infections may be used cooperatively to ensure efficient protection during biological warfare.

As part of the body's natural defense against antigens, the white blood cell count increases at the onset of infection. There are several types of white blood cells including neutrophils, lymphocytes, monocytes, eosinophils and basofils. Lymphocytes create antibodies that attack the invaders and mark them for destruction by the neutrophils and macrophages. In an individual without chronic diseases (such as tuberculosis or cancer), an increase in the percentage of lymphocytes in the overall white cell count is an indication of a viral infection. On the other side, an increase in the percentage of the neutrophils is an indication of a developing bacterial infection. Through counting of neutrophils and lymphocytes, a clear infection warning can be issued with differentiation between viral or bacterial causes.

The first clinical symptoms of infection from some bacterial agents such as bacillus anthrax appear after one to six days. In 99 percent of the cases, patients showing symptoms from anthrax cannot be treated, and will most likely die. However, if treatment is given before the first symptoms appear, most patients can be successfully treated. Accordingly, it would be highly desirable to provide an early alert and potential therapeutic intervention for hematologic abnormalities before symptoms occur. In many cases, such an early alert and treatment may greatly improve the outcome for many patients.

BRIEF DESCRIPTION OF THE DRAWING

FIG. 17a is another version of the cartridge where the liquid devices and operations occur on cartridge;

FIGS. 19a and 19b reveal an application in a microfluidic circuit of mesopumps and mesovalves embedded in a chip, card or cartridge 14;

FIG. 29 is similar to FIG. 27, except it has the flow sensor off the cartridge and has a pressure chamber;

FIG. 30 is similar to FIG. 29, except the flow sensor is on the cartridge;

FIG. 33 is similar to FIG. 30, except the components are shown off the cartridge.

DESCRIPTION

Figure 1:
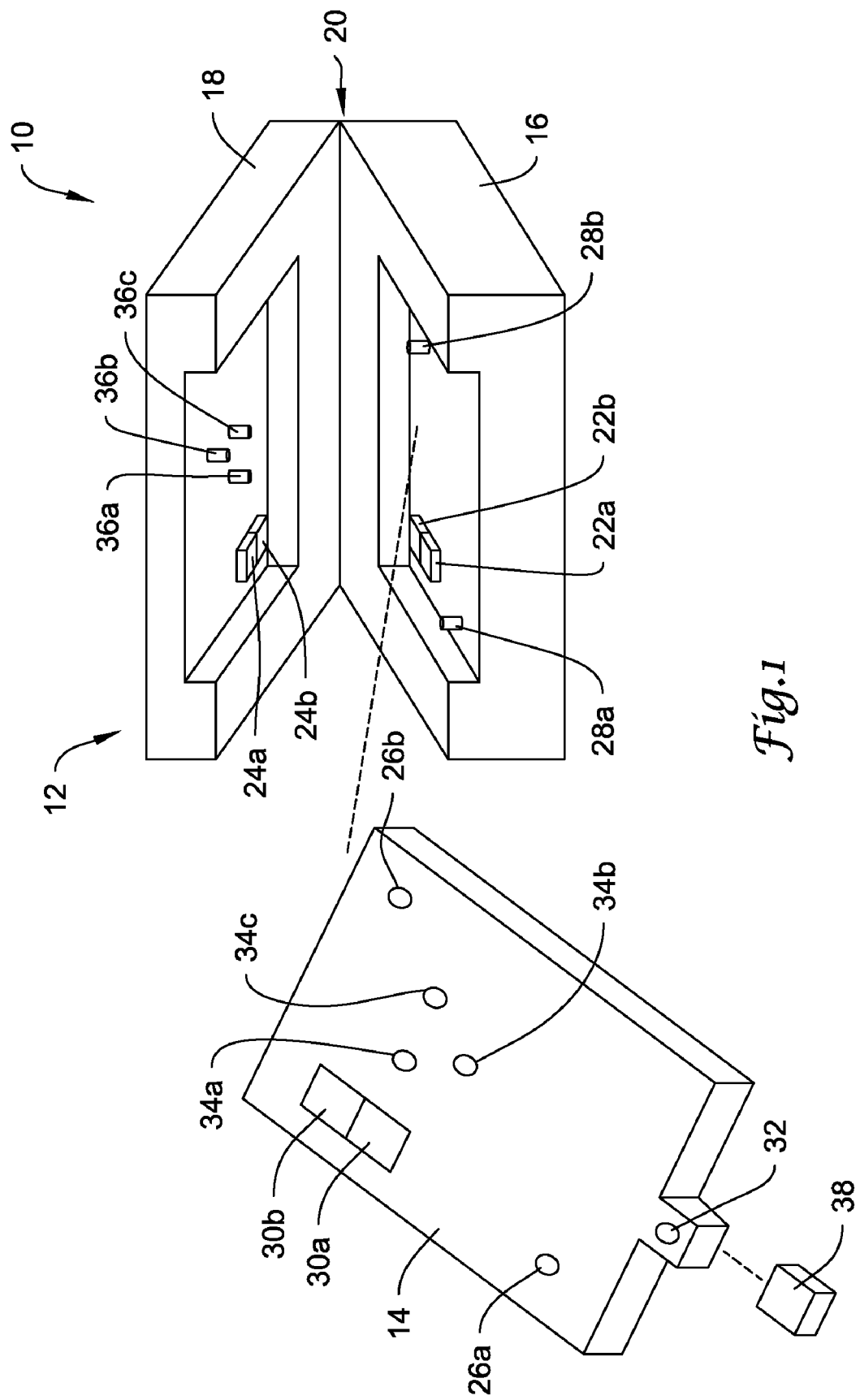
FIG. 1 is a perspective view of an illustrative portable cytometer in accordance with the present invention.

In an illustrative example of the present invention, a portable miniaturized cytometer may be provided for identifying and/or counting selected particles in a fluid sample such as a blood sample. One illustrative miniaturized portable cytometer includes a fluid receiver for receiving the fluid sample. One or more reservoirs are provided for storing supporting fluids such as lyse and sheath fluids. For many commercial flow cytometer systems, a precision fluid driving system is used for providing precise pressures to the fluids. A limitation of this approach is that precision fluid driving systems can be bulky, complex and may require significant power.

To avoid many of these limitations, an illustrative example uses a non-precision fluid driver that is controlled by a closed loop feedback path. The non-precision fluid driver is coupled to the fluid receiver and the various supporting fluid reservoirs, and applies separate pressures to the sample fluid and the supporting fluids. To control the velocity of the sample fluid and the supporting fluids, one or more valves are coupled to the fluid driver. The valves are used to regulate the non-precision pressures that are applied to the sample fluid and the supporting fluids by the non-precision fluid driver.

To complete the feedback loop, flow sensors are provided downstream of the fluid driver to measure the fluid velocity of the sample fluid and the supporting fluids. A controller or processor receives the signals from the flow sensors, and adjusts the appropriate valves so that the desired fluid velocities of the sample fluid and supporting fluids are achieved. The flow sensors are preferably thermal anemometer type flow sensors.

In one illustrative example, the non-precision fluid driver is manually powered. A manually powered fluid driver may include, for example, a bulb with check valve or a plunger. In either case, the manually generated pressure is preferably provided to a first pressure chamber. A first valve is then provided for controllably releasing the pressure in the first pressure chamber to a second pressure chamber. A second valve may be provided in the second pressure chamber for controllably venting the pressure in the second pressure chamber. The controller opens the first valve when the fluid flow in the downstream fluid stream drops below a first predetermined value and opens the second valve when the fluid flow in the downstream fluid stream increases above a second predetermined value. Each valve is preferably an array of electrostatically actuated microvalves that are individually addressable and controllable.

The controlled sample fluid and supporting fluids are provided to a fluidic circuit. The fluidic circuit may perform hydrodynamic focusing, which causes the desired particles to fall into single file along a core stream surrounded by a sheath fluid. One or more light sources or light source arrangements provide light through the flow stream, and one or more light detectors or light detector arrangements detect the scatter profile and fluorescence of the particles in the flow stream. An arrangement may have one or more light sources and/or one or more light detectors. An arrangement may include a single optical device or element or an array of such items. A processing block uses the output signals from the light detectors to identify and/or count selected particles in the core stream.

The miniaturized portable cytometer may be provided in a housing sufficiently small to be appropriately and comfortably "wearable" on a person. In one illustrative example of the invention, the housing is sized similar to a wrist watch. The wearable housing may include, for example, a base, a cover, and a hinge that secures the base to the cover. The non-precision fluid driver and regulating valves may be incorporated into the cover, while the fluid reservoirs, flow sensors and fluidic circuit may be incorporated into a removable cartridge (or "card" as it may sometimes be referred to) that is inserted into the housing. The fluidic circuit may dilute the blood sample, perform red cell lysing, and perform hydrodynamic focusing for flow and core stream formation. The light sources may be situated in either the base or the cover, and aligned with the flow stream of the removable cartridge. The light detectors are preferably provided generally opposite the light sources. The processor and batteries may be provided in either the base or the cover of the housing.

The light source may include one or a linear array of first light sources along a first light source axis. The first light source axis may be rotated relative to the central axis of the flow stream. A lens may be provided adjacent each light source to focus the light at the particles in the core stream. A detector or set of light detectors may then be placed in-line with the light source or each of the light sources. Such an arrangement can be used to determine, for example, the alignment and width of the core stream within the flow stream. If the core stream of particles is not in proper alignment, the controller can adjust the fluid velocity of the sample fluid or one of the supporting fluids to bring the core stream into alignment. The light detector or set of light detectors may also be used to detect the velocity and size of each particle, as well as the number of particles.

Another light source or set of the light sources may be provided along second light source axis. A lens may be provided adjacent each light source to focus the light at the particles in the core stream. A second detector or set of light detectors may then be placed on either side of the in-line position of each light source for measuring the small angle scattering (SALS) produced by selected particles in the flow stream.

The second light source or set of light sources may also be used in conjunction with the first set of light sources to determine the time-of-flight or velocity of the particles in the flow stream. By knowing the velocity of the particles, small variations in the flow rate caused by the fluid driver can be minimized or removed by the controller.

A third light source or set of light sources may be provided along a third light source axis. A lens may be provided adjacent each light source to provide collimated light to the flow stream. An annular light detector or detectors may then be placed opposite the light source or light sources for measuring the forward angle scattering (FALS) produced by the selected particles in the flow stream. Each of the first, second and third light sources or sets of light sources may include an array of lasers such as vertical cavity surface emitting lasers (VCSELs) fabricated on a common substrate. Each of the first, second and third detectors or sets of light detectors may include a photo detector or an array of photo detectors such as p-i-n photodiodes, GaAs photodiodes with integrated FET circuits, resonant cavity photo detectors (RCPDs), or any other suitable light detectors.

The selected particles are preferably neutrophils and/or lymphocytes white blood cells. By examining the scatter profile of each particle, the miniaturized portable cytometer of the present invention identifies and counts the neutrophils and lymphocytes in a blood sample, and provides a clear infection warning with differentiation between viral and bacterial causes.

Another part of the invention uses of fluorescence to further identify and analyze various white cells. Antibodies may be associated with particular white blood cells. The antibodies have markers or tags attached to them. These white blood cells may be impinged with light which causes their associated markers or tags to fluoresce and emit light. The light may be collected, filtered as needed, and directed to one or more photo detectors. This detection may be used to identify and monitor specific subclasses of white cells and blood-based proteins, among other things.

This miniaturized portable cytometer may have two optical detection subsystems—scattering and fluorescing. It also has a low power electronic system, a compact fluid driving system, and may use direct/unprocessed blood samples and disposable microfluidic cartridges, FIG. 1 is a perspective view of an illustrative miniaturized portable cytometer in accordance with the present invention. The cytometer is generally shown at 10, and includes a housing 12 and a removable or replaceable cartridge 14. The illustrative housing 12 includes a base 16, a cover 18, and a hinge 20 that attaches the base 16 to the cover 18. The base 16 includes light sources 22a and 22b, associated optics and the necessary electronics for operation of the cytometer. The cover 12 includes a manual pressurizing element, pressure-chambers with control microvalves, and light detectors 24a and 24b with associated optics.

The removable cartridge 14 preferably receives a sample fluid via a sample collector port 32. A cap 38 may be used to protect the sample collector port 32 when the removable cartridge 14 is not in use. The removable cartridge 14 may perform blood dilution, red cell lysing, and hydrodynamic focusing for core formation. The removable cartridge 14 may be constructed similar to the fluidic circuits available from Micronics Technologies, some of which are fabricated using a laminated structure with etched channels.

The removable structure or cartridge 14 is inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 also preferably includes transparent flow stream windows 30a and 30b, which are in alignment with the arrays of the light sources 22a and 22b, and light detectors 24a and 24b. When the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 may provide blood dilution, red cell lysing, and hydrodynamic focusing for core formation. The light sources 22a and 22b, light detectors 24a and 24b and associated control and processing electronics may perform differentiation and counting of white blood cells based on light scattering fluorescent signals. Rather than using a hinged construction for the housing 12, it is contemplated that a sliding cartridge slot or any other suitable construction may be used.

Figure 2:
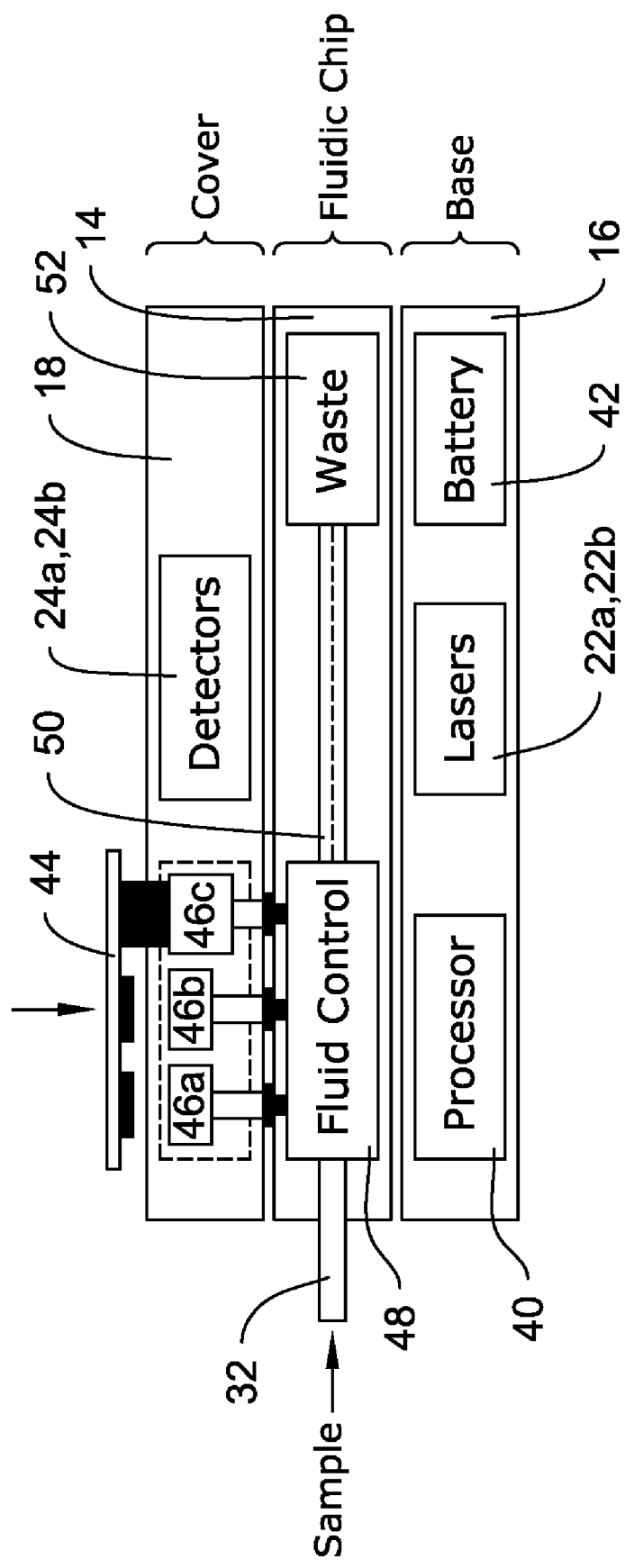
FIG. 2 is a schematic view of the illustrative portable cytometer of FIG. 1.

FIG. 2 is a schematic view of the illustrative cytometer of FIG. 1. As above, the base 16 may include light sources 22a and 22b, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and light detectors 24a and 24b with associated optics.

The removable cartridge 14 may receive a sample fluid via the sample collector port 32. When pressurized by the cover 18, the removable cartridge 14 may perform blood dilution, red cell lysing, and hydrodynamic focusing for core formation in the present device. Once formed, the core may be provided down a flow stream path 50, which passes the flow stream windows 30a and 30b of FIG. 1. The light sources 22a and 22b, and associated optics in the base provide light through and to the core stream via the flow stream windows 30a and 30b. The light detectors 24a and 24b, and associated optics receive scattered and non-scattered light from the core, also via the flow stream windows 30a and 30b, respectively. The controller or processor 40 receives output signals from the detectors 24a and 24b, and differentiates, identifies and counts selected white blood cells that are present in the core stream.

It is contemplated that the removable cartridge 14 may include a fluid control block 48 for helping control the velocity of each of the fluids. In the illustrative example, the fluid control block 48 includes flow sensors for sensing the velocity of the various fluids and reports the velocities to the controller or processor 40. The controller or processor 40 may then adjust the microvalves associated with pressure-chambers 46a, 46b and 46c to achieve the desired pressures and thus desired fluid velocities for proper operation of the cytometer.

Because blood and other biological waste can spread disease, the removable cartridge 14 preferably has a waste reservoir 52 downstream of the flow stream windows 30a and 30b. The waste reservoir 52 receives and stores the fluid of the flow stream in the removable cartridge 14. When a test is completed, the removable cartridge may be removed and disposed of, preferably in a container compatible with biological waste.

Figure 3:
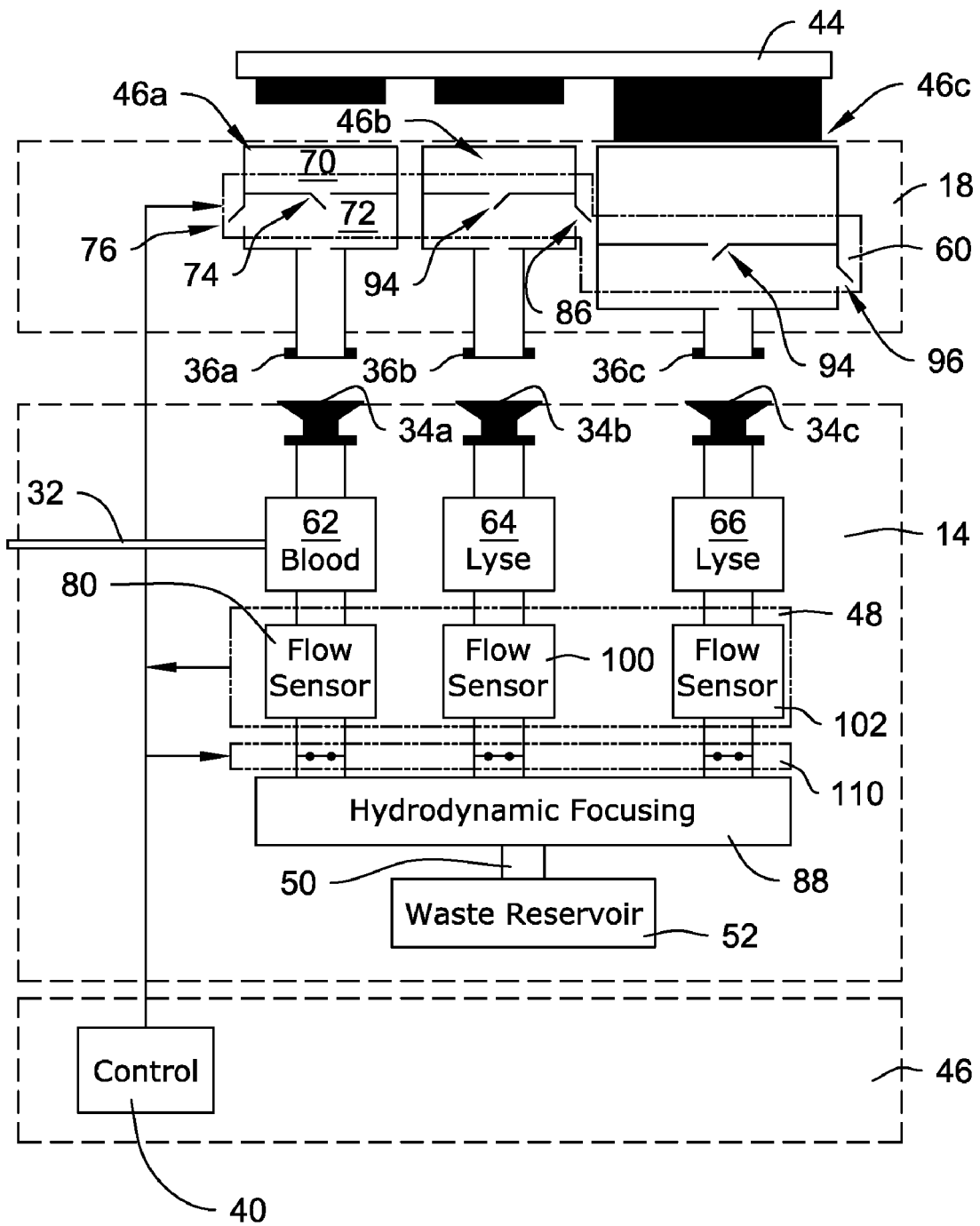
FIG. 3 is a more detailed schematic diagram showing the cytometer of FIG. 2 with the cover not yet depressed.
Figure 4:
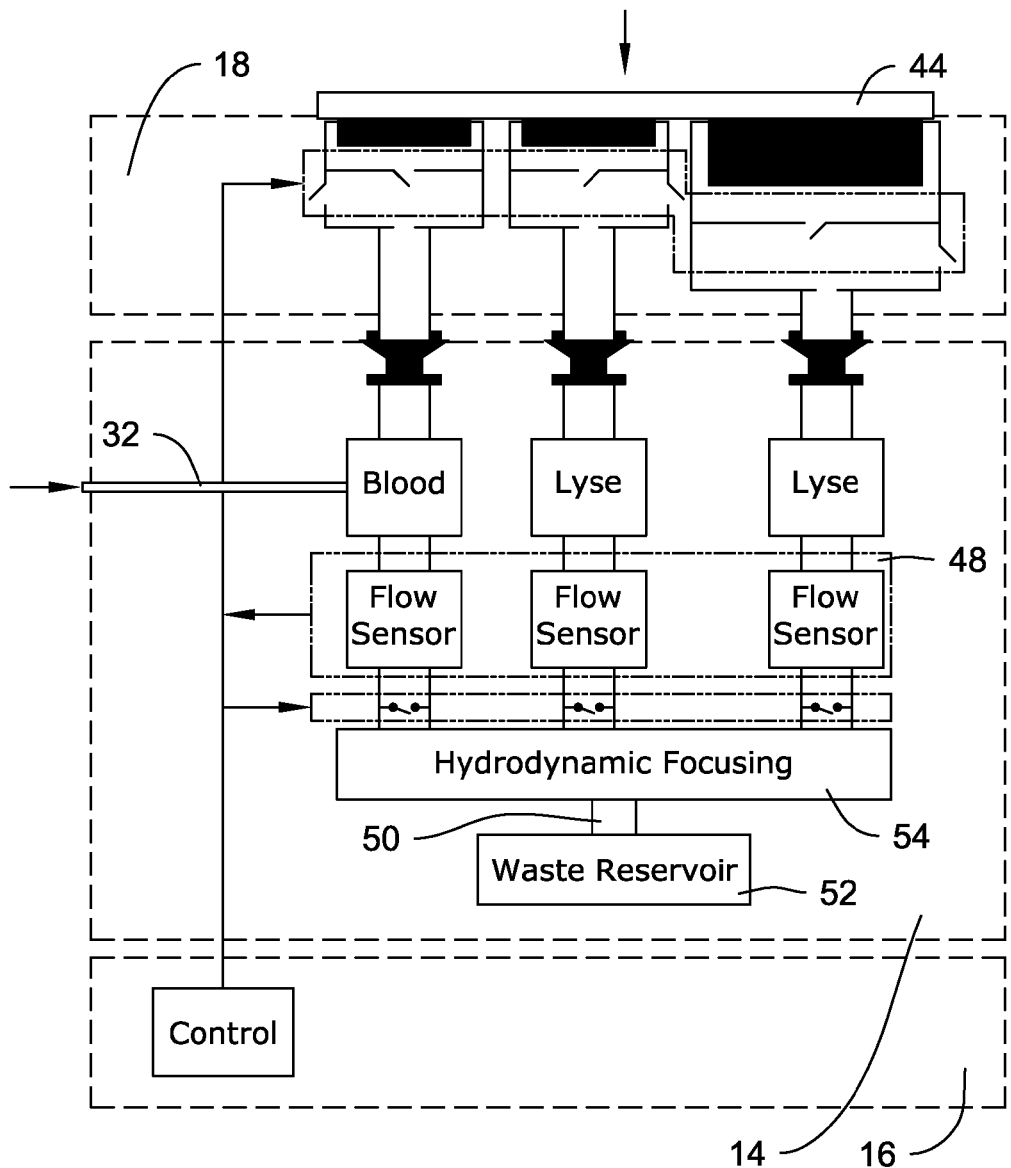
FIG. 4 is a more detailed schematic diagram showing the cytometer of FIG. 2 with the cover depressed.

FIG. 3 is a more detailed schematic diagram showing the cytometer of FIG. 2 with the cover 18 not yet depressed. FIG. 4 is a more detailed schematic diagram showing the cytometer of FIG. 2 with the cover depressed. The cover 18 is shown having a manual pressurizing element 44, pressure-chambers 46a, 46b and 46c, and control microvalves generally shown at 60. The light sources and detectors are not shown in these Figures.

There are three pressure chambers 46a, 46b and 46c, one for each fluid to be pressurized. In the illustrative example, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve is preferably an array of electrostatically actuated microvalves that are individually addressable and controllable, as described in, for example, co-pending U.S. patent application Ser. No. 09/404,560, entitled "Addressable Valve Arrays for Proportional Pressure or Flow Control", and incorporated herein by reference. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 are preferably filled before the removable cartridge 14 is shipped for use, while the blood reservoir 62 is filled from sample collector port 32. A blood sample may be provided to the sample collector port 32, and through capillary action, the blood sample is sucked into the blood reservoir 62. Once the blood sample is in the blood reservoir 62, the cover 18 may be closed and the system may be pressurized.

A flow sensor may be provided in-line with each fluid prior to hydrodynamic focusing. Each flow sensor 80, 100 and 102 may measure the velocity of the corresponding fluid. The flow sensors may be thermal anemometer type flow sensors and/or microbridge type flow sensor. Microbridge flow sensors are described in, for example, U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 5,050,429, all of which are incorporated herein by reference. An output signal from each flow sensor 80, 100 and 102 is provided to controller or processor 40.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If too much pressure builds up in the secondary pressure chambers, the corresponding vent valves 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another illustrative example of the invention, downstream valves 110 are opened by mechanical action when the cover is closed.

Figure 5:
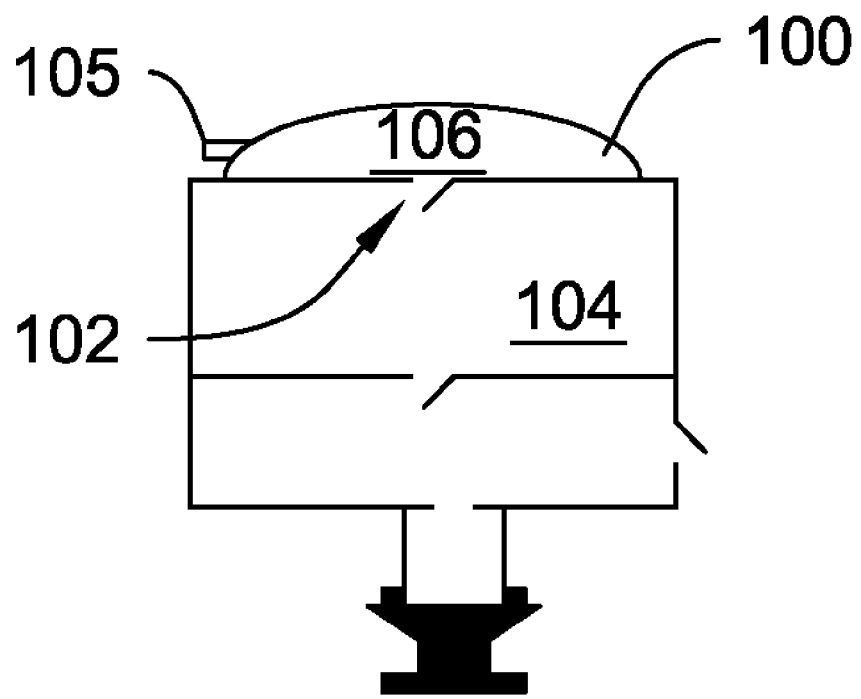
FIG. 5 is a schematic diagram showing an illustrative manual fluid driver having a bulb and check valve.

FIG. 5 is a schematic diagram showing an illustrative manual fluid driver having a bulb 100 and check valve 102. The check valve 102 is preferably a one way valve that allows air in but not out of the first pressure chamber 104. When the bulb 100 is depressed, the air in the interior 106 of the bulb 100 is forced through the check valve 102 and into the first pressure chamber 104. Preferably, another one-way vent valve 105 is provided that allows air in from the atmosphere but not out of the interior 106 of the bulb 100. Thus, when the bulb is released, the one-way vent valve 105 may allow replacement air to flow into bulb 100.

Rather than using a manually operated fluid driver, it is contemplated that any relatively small pressure source may be used including, for example, an electrostatically actuated mesopump. One such mesopump is described in, for example, U.S. Pat. No. 5,836,750 to Cabuz, which is incorporated herein by reference.

Figure 6:
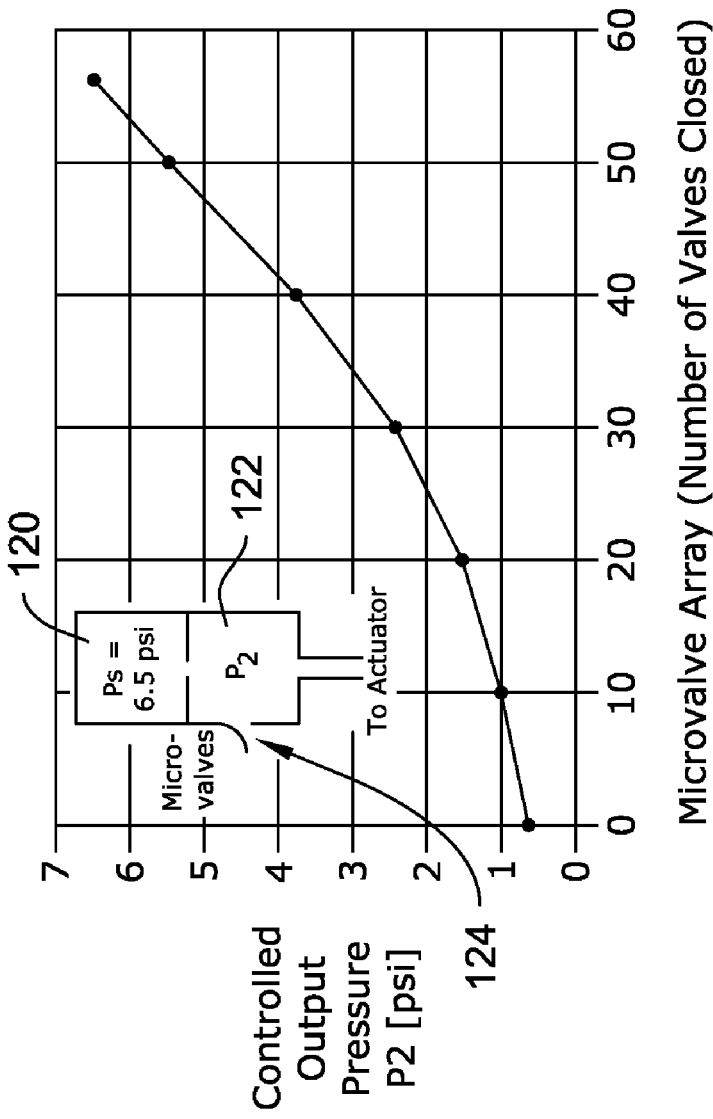
FIG. 6 is a graph showing proportional pressure control of an addressable array of microvalves.

FIG. 6 is a graph showing proportional pressure control produced by an 8×7 addressable array of microvalves. To create the graph shown in FIG. 6, 6.5 psi was applied to a first pressure chamber 120. A small opening was provided to a second pressure chamber 122. The microvalves are shown at 124, and vent the pressure in the second pressure chamber 122. By changing the number of addressable microvalves that are closed, the pressure in the second pressure chamber can be changed and controlled. In the graph shown, the pressure in the second pressure chamber 122 could be changed from about 0.6 psi, when zero of the 8×7 array of microvalves close, to about 6.5 psi, when all of the 8×7 array of microvalves are closed. These low power, micromachined silicon microvalves can be used for controlling pressures up to 10 psi and beyond.

Figure 7:
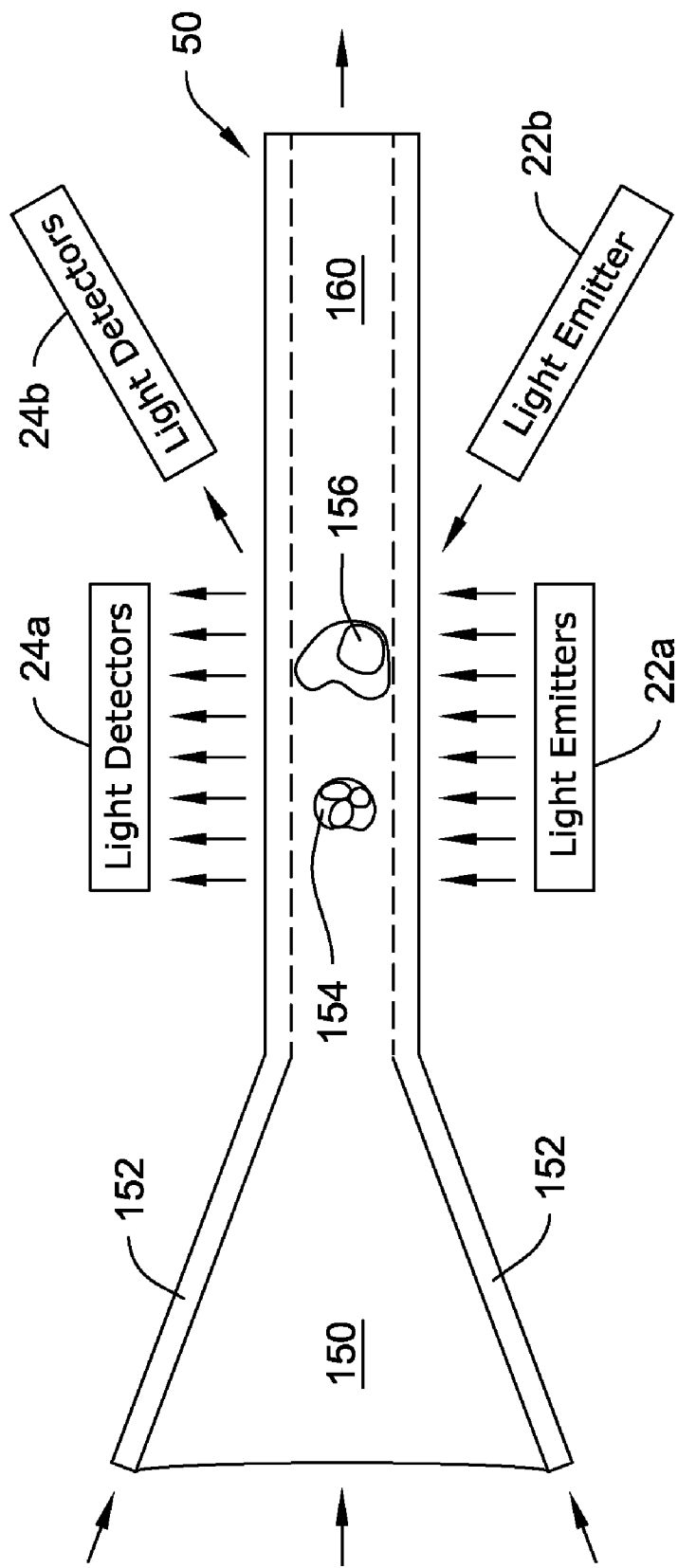
FIG. 7 is a schematic diagram showing the formation of a flow stream by a flow mechanism block 88 of FIG. 3.

FIG. 7 is a schematic diagram showing the formation of a flow stream and core by a flow mechanism block 88, which may provide hydrodynamic focusing, of FIG. 3. The block 88 may receive blood, lyse and sheath at controlled velocities from the fluid driver. The blood may be mixed with the lyse, causing the red blood cells to be removed. The lysing solution may have a pH lower than that of the red blood cells. This is often referred to as red cell lysing or lyse-on-the-fly. The remaining white blood cells are provided down a central lumen 150, which is surrounded by sheath fluid to produce a flow stream 50. The flow stream 50 includes a core stream 160 surrounded by the sheath fluid 152. The dimensions of the channel are reduced as shown so that the white blood cells 154 and 156 are in single file. The velocity of the sheath fluid is preferably about 9 times that of the core stream 160. However, the velocity of the sheath fluid and core stream 160 remain sufficiently low to maintain laminar flow in the flow channel.

Light emitters 22a and 22b, and associated optics are preferably provided adjacent one side of the flow stream 50. Light detectors 24a and 24b, and associated optics are provided on another side of the flow stream 50 for receiving the light from the light emitters 22a and light from fluorescing particles via the flow stream 50. The output signals from the light detectors 24a and 24b are provided to controller or processor 40, wherein they are analyzed to identify and/or count selected white blood cells in the core stream 160.

Figure 8:
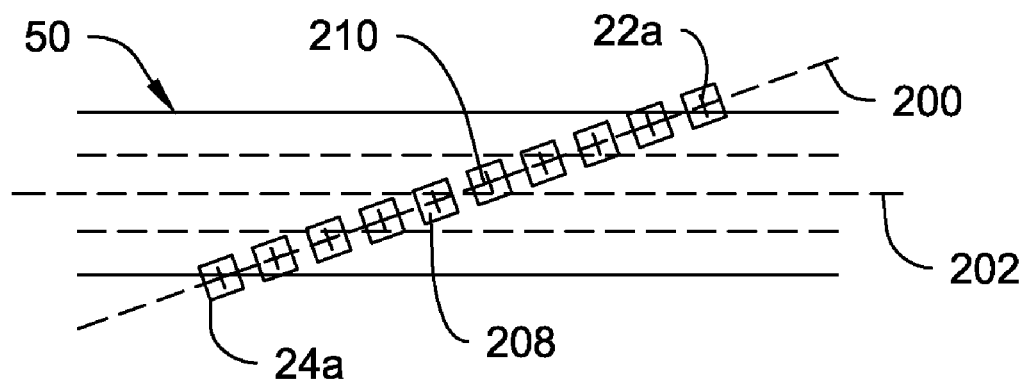
FIG. 8 is a schematic diagram showing an array of light sources and an array of light detectors for analysis of the core stream of FIG. 7.

FIG. 8 is a schematic diagram showing an array 22a of light sources and an array 24b of light detectors for analysis of the core stream 160 via scattering of FIG. 7. The light sources are shown as "+" signs and the detectors are shown at boxes. In the example shown, the array of light sources is provided adjacent one side of the flow stream 50, and the array of light detectors is provided adjacent the opposite side of the flow stream. Each of the light detectors is preferably aligned with a corresponding one of the light sources. The array of light sources and the array of light detectors are shown arranged along a light source axis 200 that is slightly rotated relative to the axis 202 of the flow stream 50.

The array 22a of light sources is preferably an array of lasers such as vertical cavity surface emitting lasers (VCSELs) fabricated on a common substrate. Because of their vertical emission, VCSELs are ideally suited for packaging in compact instruments such as a miniaturized portable cytometer. Such cytometer may be wearable on a person's body. Preferably, the VCSELs are "red" VCSELs that operate at wavelengths that are less than the conventional 850 nm, and more preferably in the 670 nm to 780 nm range. Red VCSELs may have a wavelength, power and polarization characteristic that is ideally suited for scatter measurements.

Some prior art cytometer bench models use a single 9 mW edge-emitting laser with a wavelength of 650 nm. The beam is focussed to a 10×100 micron elongated shape to cover the uncertainty in particle position due to misalignment and width of the core stream. In contrast, the output power of the red VCSELs of the present invention, operating at 670 nm, is typically around 1 mW for a 10×20 micron emitter and 100-micron spacing. Thus, the total intensity of the light from a linear array of ten red VCSELs may be essentially the same as that of some prior art bench models.

Using a linear array of lasers oriented at an angle with respect to the flow axis 202 offers a number of important advantages over the single light source configuration of the prior art. For example, a linear array of lasers may be used to determining the lateral alignment of the path of the particles in the core steam. One source of uncertainty in the alignment of the particle stream is the width of the core flow, which leads to statistical fluctuations in the particle path position. These fluctuations can be determined from analysis of the detector data and can be used by the controller or processor 40 to adjust the valves of the fluid driver in order to change the relative pressures that are applied to the sample fluid and the supporting fluids to change the alignment of the selected particles in the flow stream.

To determine the lateral alignment of the cells in the fluid stream 50, the cells pass through several focussed spots produced by the linear array of VCSELs. The cells produce a drop in signal in the corresponding in-line reference detectors. The relative strengths of the signals are used by the controller or processor 40 to determine the center of the particle path and a measure of the particle width.

Figure 9:
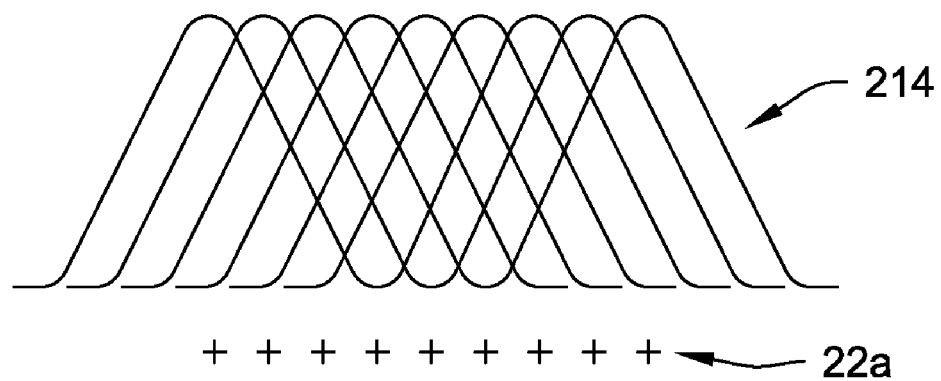
FIG. 9 is a graph showing the light intensity produced along the light source axis of FIG. 8.

For determining particle path and size, the lasers 22a are preferably focussed to a series of Gaussian spots 214 (intensity on the order of 1000 W/cm$^2$) in the plane of the core flow. The spots 214 are preferably about the same size as a white blood cell (10-12 um). Illustrative Gaussian spots 214 are shown in FIG. 9. Arrays 24a of detectors and their focussing optics are provided on the opposite side of the fluid stream 50. Lenses with fairly large F-numbers are used to provide a working space of several hundred microns for the cytometer section of the removable cartridge.

Another advantage of using a linear array 22a of lasers rather than a single laser configuration is that the velocity of each cell may be determined. Particle velocity can be an important parameter in estimating the particle size from light scatter signals. In conventional cytometry, the particle velocity is extrapolated from the pump flow rates. A limitation of this approach is that the pumps must be very precise, the tolerance of the cytometer flow chambers must be tightly controlled, no fluid failures such as leaks can occur, and no obstructions such as microbubbles can be introduced to disturb the flow or core formation.

To determine the velocity of each cell, the system may measure the time required for each cell to pass between two adjacent or successive spots. For example, and with reference to FIG. 8, a cell may pass detector 208 and then detector 210. By measuring the time required for the cell to travel from detector 208 to detector 210, and by knowing the distance from detector 208 to detector 210, the controller or processor 40 can calculate the velocity of the cell. This would be an approximate velocity measurement. This is often referred to as a time-of-flight measurement. Once the velocity is known, the time of travel through the spot on which the particle is centered (a few microseconds) may provide a measure of particle length and size.

It is contemplated that the particle velocity can also be used to help control the fluid driver. To reduce the size, cost and complexity of the present invention, the replaceable cartridge of FIG. 1 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed above can be used by the controller or processor 40 to adjust the controlled pressures applied to the blood, lyse and sheath fluid streams such that the particles in the core stream have a relatively constant velocity.

To further evaluate the cell size, it is contemplated that laser beams may be focused both along the cell path and across the cell path. Additionally, multiple samples across the cell may be analyzed for texture features, to correlate morphological features to other cell types. This may provide multiple parameters about cell size that may help separate cell types from one another.

Another advantage of using a linear array 22a of lasers rather than a single layer configuration is that a relatively constant light illumination may be provided across the flow channel. This is accomplished by overlapping the Gaussian beams 214 from adjacent VCSELs 22a, as shown in FIG. 9. In prior art single laser systems, the light illumination across the flow channel typically varies across the channel. Thus, if a particle is not in the center of the flow channel, the accuracy of subsequent measurements may be diminished.

Figure 10:
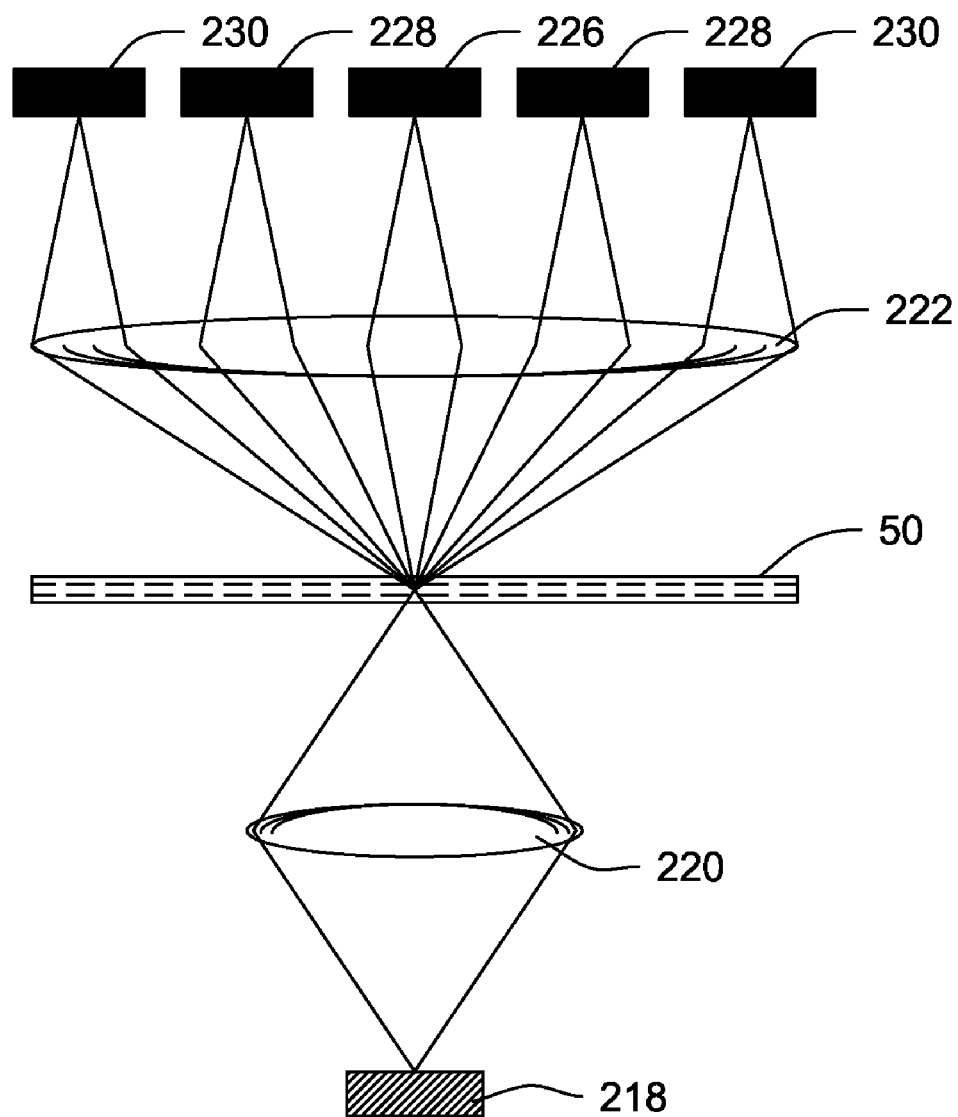
FIG. 10 is a schematic diagram showing an illustrative light source and detector pair of FIG. 8.

To perform the above described measurements, each detector 24a in FIG. 8 may be a single in-line detector. To measure FALS and SALS scatter, however, each detector 24a may further include two annular detectors disposed around the in-line detector, as shown in FIG. 10. Referring to FIG. 10, a VCSEL 218 is shown providing light in an upward direction. The light is provided through a lens 220, which focuses the light to a Gaussian spot in the plane of the core flow. Lens 220 may be a microlens or the like, which is either separate from or integrated with the VCSEL 218. The light passes through the core flow, and is received by another lens 222, such as a diffractive optical element. Lens 222 provides the light to in-line detector 226 and annular detectors 228 and 230. The in-line detector 226 detects the light that is not significantly scattered by the particles in the core stream. Annular detector 228 detects the forward scatter (FALS) light, and annular detector 230 detects the small angle scatter (SALS) light.

Figure 11:
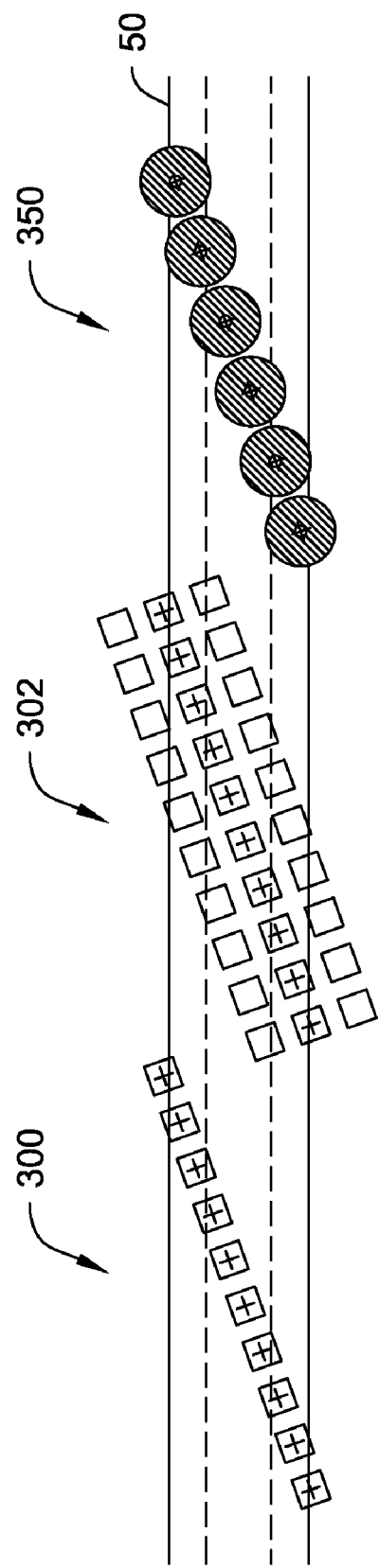
FIG. 11 is a schematic diagram showing three separate arrays of light sources and detectors, each positioned along a different light source axis that is slightly rotated relative to the central flow axis of the flow stream of FIG. 7.

FIG. 11 shows another illustrative example of the present invention that includes three separate arrays of light sources and light detectors. Each array of light sources and light detectors are positioned along a different light source axis that is slightly rotated relative to the central flow axis of the flow stream. By using three arrays, the optics associated with each array may be optimized for a particular application or function. For detecting small angle scattering (SALS), laser light that is well-focussed on the plane of the core flow is desirable. For detecting forward scattering (FALS), collimated light is desirable.

Referring specifically to FIG. 11, a first array of light sources and light detectors is shown at 300. The light sources and light detectors are arranged in a linear array along a first light source axis. The first light source axis is rotated relative to the flow axis of the flow stream. The light sources and light detectors may be similar to that described above with respect to FIG. 8, and preferably are used to measure, for example, the lateral alignment of the cells in the flow stream, the particle size, and the velocity of the particles.

Figure 11A:
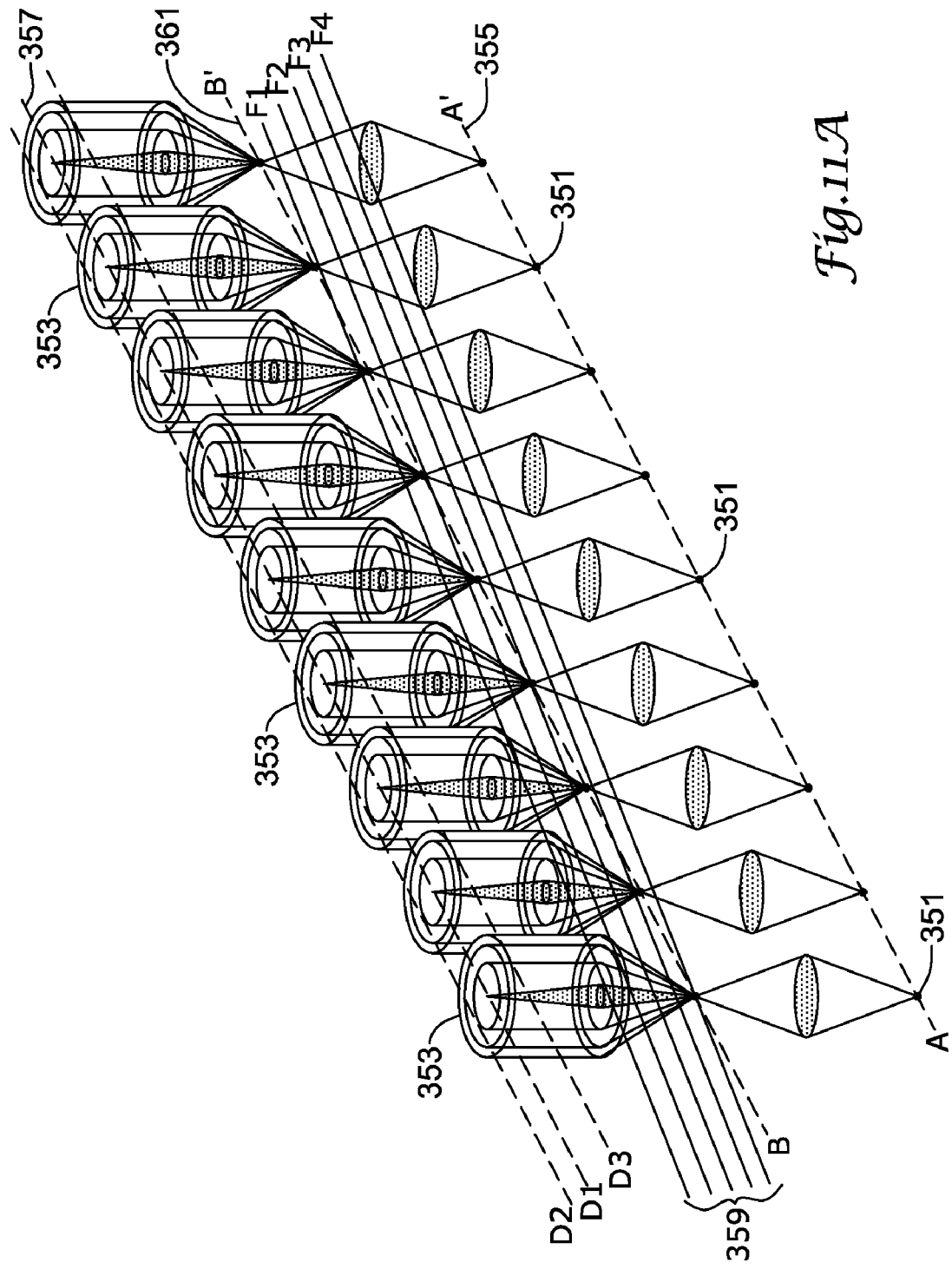
FIG. 11a is a three dimensional illustration of an array of light sources and an array of light detectors positioned along a light source and detector axis that is not parallel to the central flow axis of the flow stream.

FIG. 11a is a three dimensional illustration of an array of light sources 351 and an array of light detectors 353 positioned along a light source axis 355 and detector axis 357, respectively, which are not parallel (i.e., are statically rotated) relative to the central flow axis of the flow stream 359. Axes 355, 357 and 361 are typically parallel to one another. Line 361 is an axis of light spots across flow stream 359.

Figure 12:
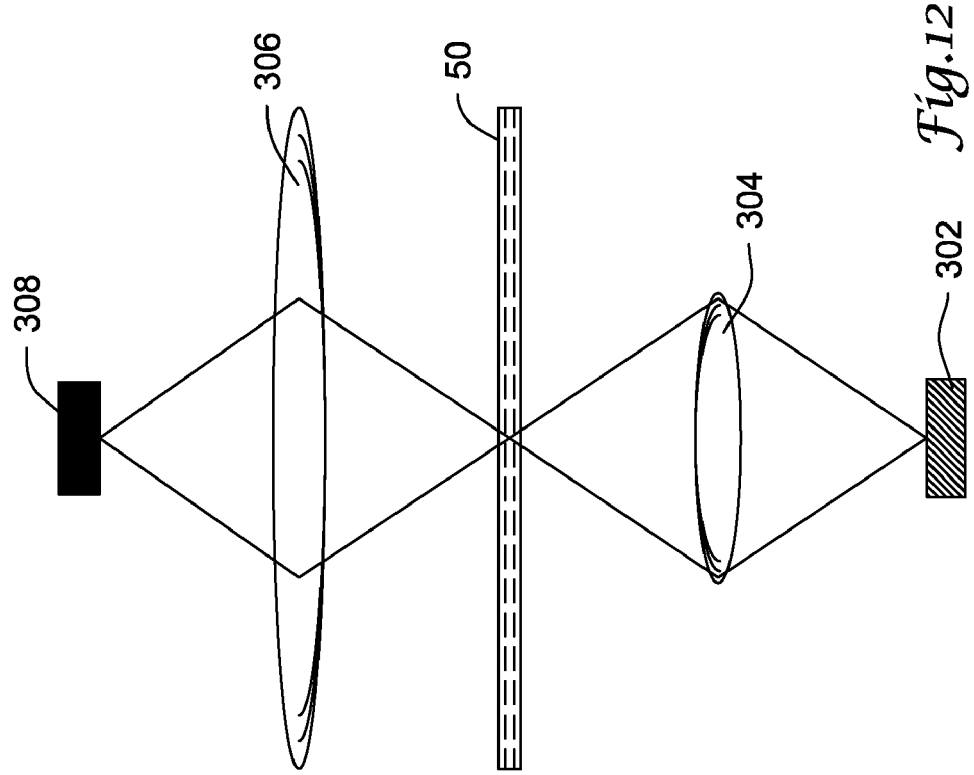
FIG. 12 is a schematic diagram showing an illustrative light source and detector pair of the first array shown in FIG. 11.

FIG. 12 is a schematic diagram showing an illustrative light source and detector pair of the first array 300 shown in FIG. 11. A VCSEL 302 is shown providing light in an upward direction. The light is provided through a lens 304, which focuses the light to a Gaussian spot in the plane of the core flow. The light passes through the core flow, and is received by another lens 306. Lens 306 provides the light to in-line detector 308. The in-line detector 308 detects the light that is not significantly scattered by the particles in the core stream.

A second array of light sources and light detectors is shown at 310. The light sources are arranged in a linear array along a second light source axis that is rotated relative to the flow axis of the flow stream. The light detectors include three linear arrays of light detectors. One array of light detectors is positioned in line with the linear array of light sources. The other two linear arrays of light detectors are placed on either side of the in-line array of light detectors, and are used for measuring the small angle scattering (SALS) produced by selected particles in the flow stream.

Figure 13:
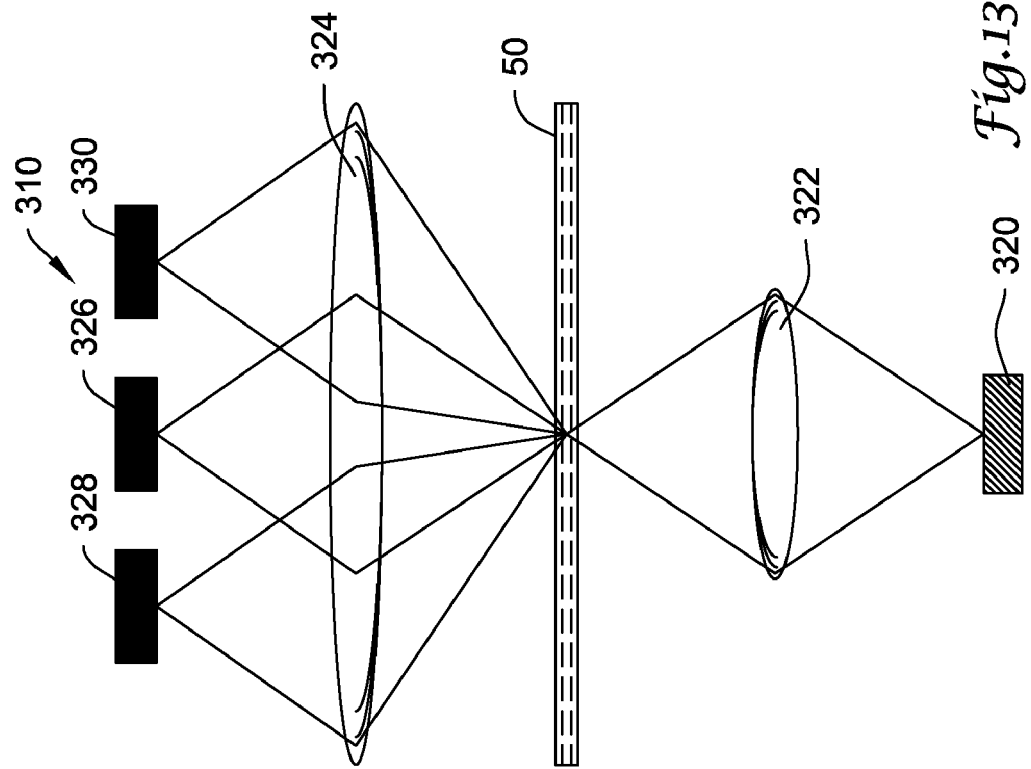
FIG. 13 is a schematic diagram showing an illustrative light source and detector pair of the second array shown in FIG. 11.

FIG. 13 is a schematic diagram showing an illustrative light source and corresponding detectors of the second array shown in FIG. 11. A VCSEL 320 is shown providing light in an upward direction. The light is provided through a lens 322, which focuses the light to a Gaussian spot in the plane of the core flow. The light passes through the core flow, and is received by another lens 324, such as a diffractive optical element (DOE) 324. Lens 324 provides the light to the in-line detector 326 and the two corresponding light detectors 328 and 330 placed on either side of the in-line light detector 326.

The in-line detector 326 may be used to detect the light that is not significantly scattered by the particles in the core stream. Thus, the in-line linear array of light detectors of the second array 302 may be used to provide the same measurements as the in-line array of detectors of the first array 300. The measurements of both in-line arrays of detectors may be compared or combined to provide a more accurate result. Alternatively, or in addition, the in-line detectors of the second array 302 may be used as a redundant set of detectors to improve the reliability of the cytometer.

It is contemplated that the in-line detectors of the second array 302 may also be used in conjunction with the in-line detectors of the first array 300 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

Light detectors 328 and 330 of FIG. 13 are used to measure the small angle scattering (SALS) produced by selected particles in the flow stream. The light detectors 328 and 330 are therefore preferably spaced sufficiently from the in-line detector 326 to intercept the small angle scattering (SALS) produced by selected particles in the flow stream.

Referring back to FIG. 11, a third array of light sources and light detectors 350 is preferably provided to measure the forward angle scattering (FALS) produced by selected particles in the flow stream. The light sources are arranged in a linear array along a third light source axis that is rotated relative to the flow axis of the flow stream. Each light source preferably has a corresponding light detector, and each light detector is preferably annular shaped with a non-sensitive region or a separate in-line detector in the middle. The annular shaped light detectors are preferably sized to intercept and detect the forward angle scattering (FALS) produced by selected particles in the flow stream.

Figure 14:
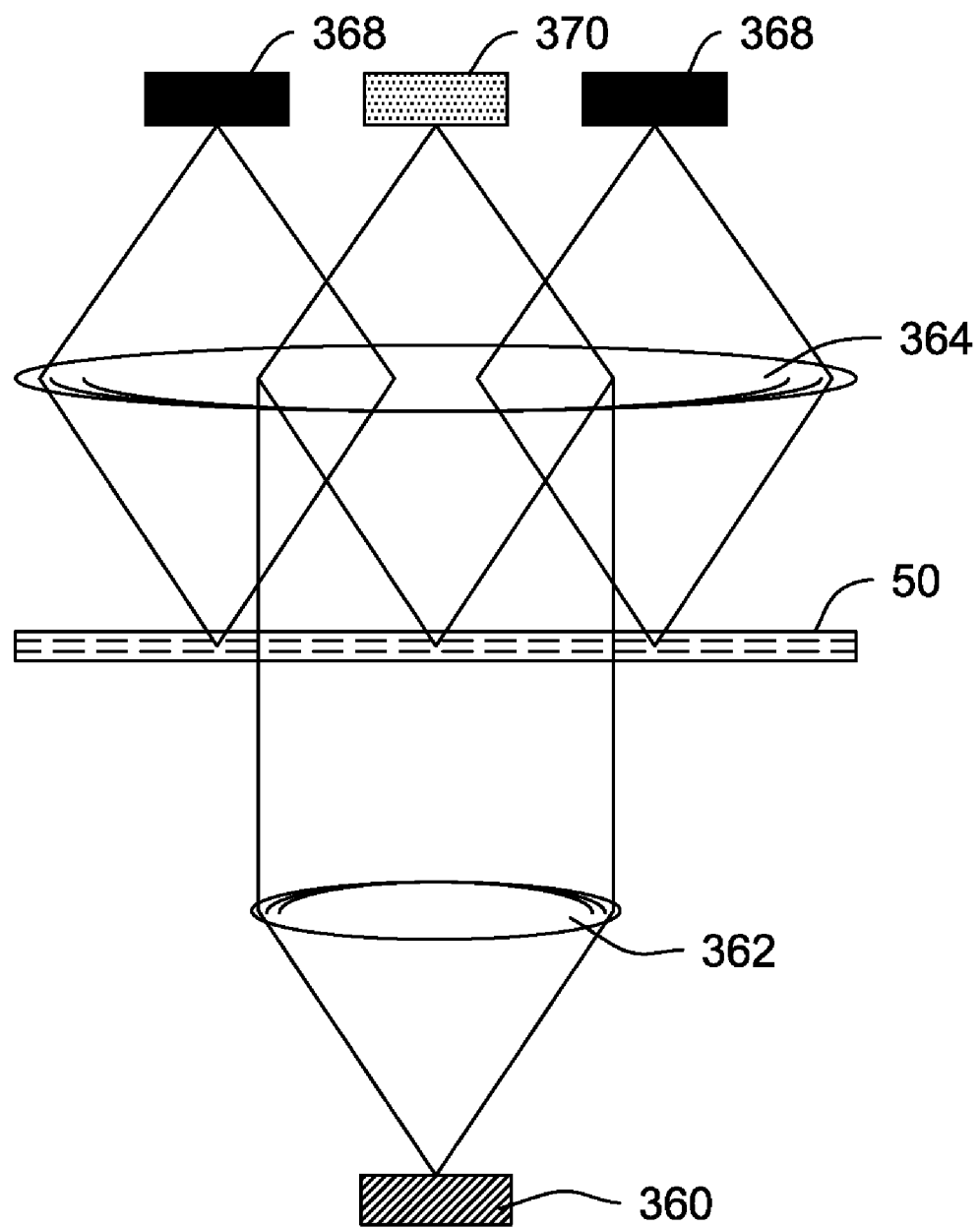
FIG. 14 is a schematic diagram showing an illustrative light source and detector pair of the third array shown in FIG. 11.

FIG. 14 is a schematic diagram showing an illustrative light source and detector pair of the third array of light sources and light detectors 350 shown in FIG. 11. A VCSEL 360 is shown providing light in an upward direction. The light is provided through a lens 362 such as a collimating lens, which provides substantially collimated light to the core flow. As indicated above, collimated light is desirable for detecting forward scattering (FALS) light. The light passes through the core flow, and is received by another lens 364. Lens 364 provides the received light to the annular shaped detector 368.

The annular shaped detector 368 is preferably sized to intercept and detect the forward angle scattering (FALS) produced by selected particles in the flow stream. A non-sensitive region or a separate in-line detector 370 may be provided in the middle of the annular shaped detector 368. If a separate in-line detector 370 is provided, it can be used to provide the same measurement as the in-line detectors of the first array 300 and/or second array 302. When so provided, the measurements from all three in-line arrays of detectors of first array 300, second array 302 and third array 350 may be compared or combined to provide an even more accurate result. The in-line detectors of the third array 302 may also be used as another level or redundancy to improve the reliability of the cytometer.

It is contemplated that the in-line detectors of the third array 350 may also be used in conjunction with the in-line detectors if the first array 300 and/or second array 302 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

By using three separate arrays of light sources and detectors, the optics associated with each array can be optimized for the desired application. As can be seen, the optics associated with the first array 300 are designed to provide well-focussed laser light on the plane of the core flow. This helps provide resolution to the alignment, size and particle velocity measurements performed by the first array 300. Likewise, the optics associated with the second array 302 are designed to provide well-focussed laser light on the plane of the core flow. Well focussed light is desirable when measuring the small angle scattering (SALS) produced by selected particles in the flow stream. Finally, the optics associated with the third array 350 are designed to provide collimated light to the core flow. As indicated above, collimated light is desirable when measuring forward angle scattering (FALS) produced by selected particles in the flow stream.

Figure 15:
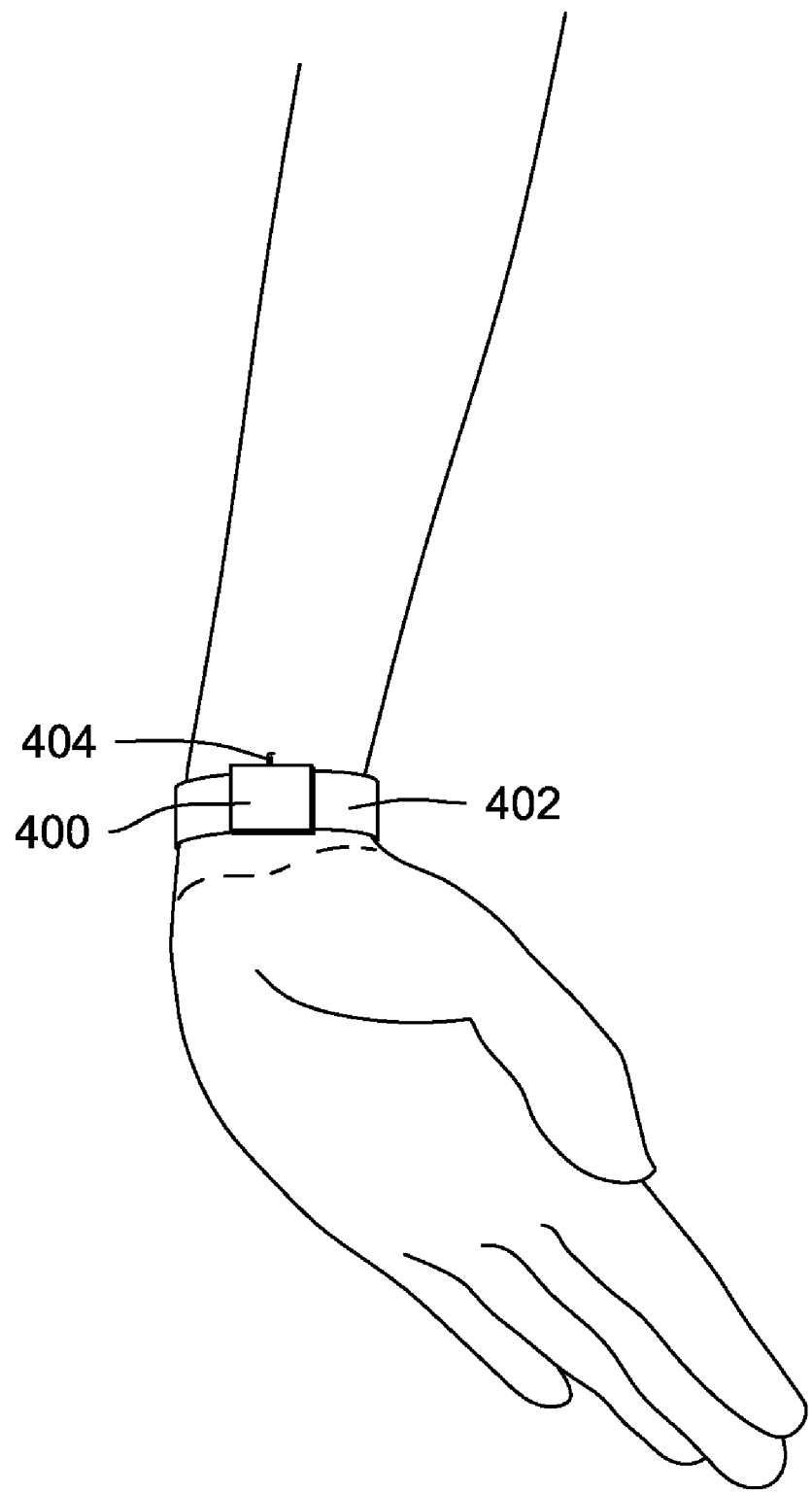
FIG. 15 is a perspective view of an illustrative example of the miniaturized portable cytometer adapted to be worn around the wrist.

FIG. 15 is a perspective view of an illustrative example of the miniaturized portable cytometer of the present invention adapted to be worn around the wrist. This cytometer 400 may be similar to that shown in FIG. 1. A band 402 secures cytometer 400 to the wrist of a user.

As indicated above, the user may obtain a removable cartridge and provide a blood sample to the sample collector port 32 (see FIG. 1) of the removable cartridge. The blood sample may be collected by, for example, a finger prick. The user may then insert the removable cartridge into the housing, and manually pressurize the system. The miniaturized portable cytometer may then provide a reading that indicates if the user should seek medical treatment. The reading may be a visual reading, an audible sound or any other suitable indicator.

Rather than obtaining the blood sample by a finger prick or the like, it is contemplated that a catheter 404 or the like may be inserted into a vein of the user and attached to the sample collector port 32. This may allow the system to automatically collect a blood sample from the user whenever a reading is desired. Alternatively, it is contemplated that the miniaturized portable cytometer may be implanted in the user, with the sample collector port 32 connected to a suitable blood supply.

Figure 16:
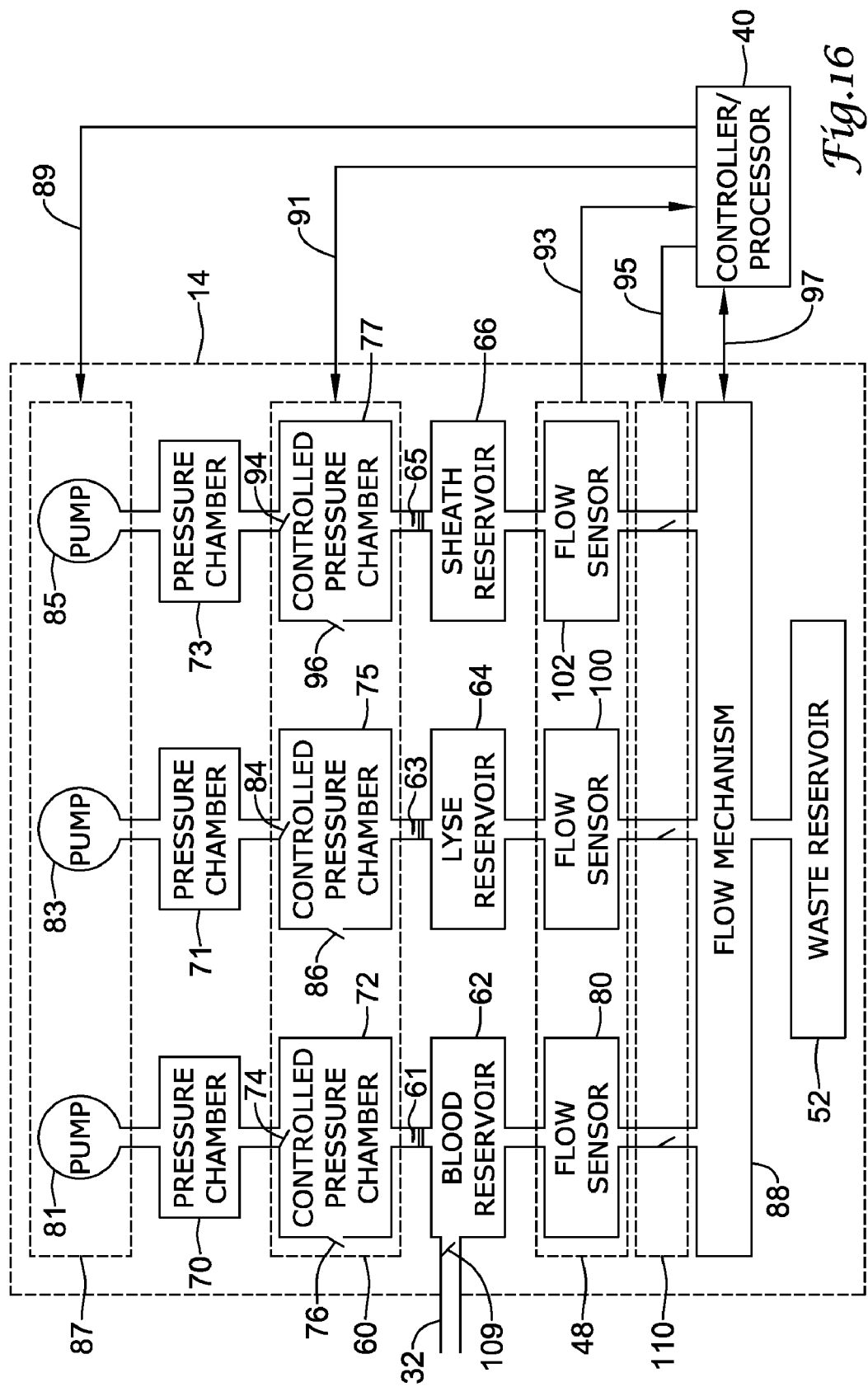
FIG. 16 reveals a disposable cytometer cartridge containing the pumps, pressure chambers, reservoirs, flow sensors, and a flow mechanism with a flow channel on the cartridge.

FIG. 16 reveals a disposable cytometer cartridge 14 containing the pumps, pressure chambers, reservoirs, flow sensors, and a flow mechanism with a flow channel. The flow mechanism may perform hydrodynamic focusing. There might be no external fluid connections on the cartridge. There may be external electrical connections from the cartridge 14 to a controller, computer or processor 40 (hereafter referred to as a processor). However, processor 40 or a portion of it may be included in the cartridge 14. Processor 40 or a portion of it may be in a form of a chip. External to cartridge 14 may be a light source or sources and detector or detectors associated with the flow channel on the cartridge 14. All of the liquids are self-contained in the cartridge except for a blood sample that is to be analyzed which is input directly to the cartridge via a port 32.

A pump 81 may pump air into a pressure chamber 70. Pump 81 may be a mesopump as described as an illustrative example by U.S. Pat. No. 5,836,750. Pump 81 may be controlled by processor 40 via a line 89 and connection block 87. The air may enter a controlled pressure chamber 72 via a valve 74. The air in chamber 72 may be controlled to be at some pre-determined pressure with mesovalves or other microvalves 74 and 76. The air may proceed into blood reservoir 62. Valve 74 may open and valve 76 may close when more air pressure is needed in chamber 72. Valve 74 may close and valve 76 may open if there is a need to reduce the air pressure in chamber 72. Valves 74 and 76 may be controlled by processor 40 via line 91 and connection block 60. Block 60 represents appropriate connections from line 91 to the valves of chamber 72. The air may proceed through a porous filter 61 on to a blood reservoir 62. Filter 61 may permit a passage of air but blocks the passage of liquid. The air may exert a controlled pressure on the liquid blood in the reservoir 62. The blood may flow from the reservoir 62 through flow sensor 80. Flow sensor 80 may provide information relating to the amount of blood flowing through the sensor via a connection block 48 and line 93 to processor 40. With the sensed blood flow information, processor 40 may send control signals to valves 74 and 76 to control the air pressure upon the liquid in the reservoir 62 so as to result in a predetermined flow rate of the blood into a flow mechanism 88 which may have a flow channel and hydrodynamic focusing.

In a similar fashion as for the blood provision, the lyse provision may have a pump 83 that pumps air into a pressure chamber 71. Pump 83 may be like pump 81. Pump 83 may be controlled by processor 40 via the line 89 and connection block 87. The air may enter a controlled pressure chamber 75. The air in chamber 75 may be controlled to be at some predetermined pressure with valves 84 and 86. The air may proceed on through a porous filter 63 to a lyse reservoir 64. Valve 84 may open and valve 86 may close when more air pressure is needed in chamber 75. Valve 84 may close and valve 86 may open if there is a need to reduce air pressure in chamber 75. Valves 84 and 86 may be controlled by processor 40 via line 91 and connection block 60. Block 60 represents an appropriate connection from line 91 to the valves of chamber 75. The air may proceed through a porous filter 63 on to a lyse reservoir 64. Filter 63 may permit a passage of air but block the passage of liquid. The air may exert a controlled pressure on the liquid lyse in the reservoir 64. The lyse may flow from the reservoir through flow sensor 100. Flow sensor 100 may provide information about the amount of lyse flowing through the sensor via a connecting block 48 and line 93 to processor 40. With the sensed lyse flow information, processor 40 may send control signals to valves 84 and 86 to control the air pressure upon the liquid in the reservoir 64 so as to result in a predetermined flow rate of the lyse into a flow focusing mechanism 88.

In a similar fashion, as for the blood and lyse provisions, the sheath provision may have a pump 85 that pumps air into a pressure chamber 73. Pump 85 may be a pump like pumps 81 and 83. Pump 85 may be controlled by processor 40 via the line 89 and connection block 87. The air may enter from chamber 73 to a controlled pressure chamber 77. The air in chamber 77 may be controlled to be at some predetermined pressure with valves 94 and 96. The air may proceed from chamber 77 through a porous filter 65 on to a sheath reservoir 66. Valve 94 may open and valve 96 may close when more air pressure is needed in chamber 77. Valve 94 may close and valve 96 may open if there is a need to reduce air pressure in chamber 77. Valves 94 and 96 may be controlled by processor 40 via line 91 and connection block 60. Block 60 represents an appropriate connection from line 91 to the valves of chamber 77. The air may exert a controlled pressure on the liquid sheath in the reservoir 66. The sheath may flow from the reservoir through flow sensor 102. Flow sensor 102 may provide information about the amount of sheath flowing through the sensor 102 via a connecting block 48 and line 93 to processor 40. With the sensed sheath flow information, processor may send signals to pump 85 and valves 94 and 96 to control the air pressure upon the sheath liquid in the reservoir 66 so as to result in a predetermined flow rate of the sheath into the flow mechanism 88. Ports, connected to an external pressurized air supply, may be implemented in lieu of pumps 81, 83 and 85 on cartridge 14 in FIG. 16.

In the flow mechanism 88, the blood from reservoir 62 may be lysed of its red blood cells and inserted with a flow channel (50) with a sheath liquid around the stream of the white cells (remaining) in the blood into a single file. The white cells and other particles may be illuminated by light sources, and light from the flow channel may be detected by detectors. The light sources and detectors may be controlled and information may be had from them via connections on line 97 between processor 40 and mechanism 88. Mechanism 88 and the flow channel are described in other places of the present description. After the blood sample along with the sheath leave the flow channel of mechanism, it may go into the waste reservoir 52.

Before the cartridge 14 is used and until its system is pressurized, a set of downstream valves 110 between reservoirs 62, 64 and 66 and mechanism 88 may be closed. Their closure and open status may be controlled by processor 40 via line 95 and connection block 110.

Figure 17B:
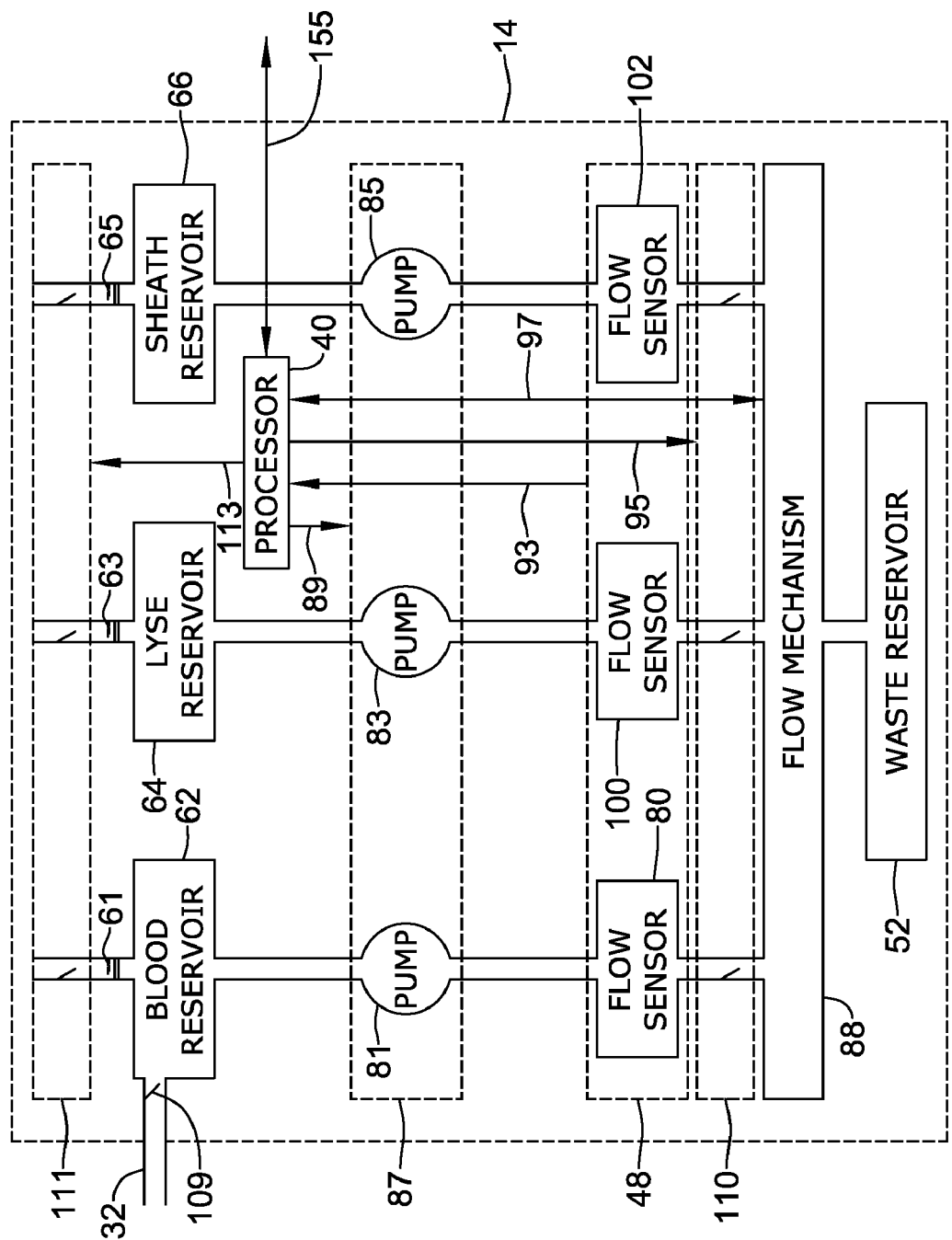
FIG. 17b is like the version of FIG. 17a except that the processor is situated in the cartridge.

FIG. 17a is another version of the cartridge 14 where all of the liquid devices and operations occur on cartridge. FIG. 17b reveals the same version as that of FIG. 17a except a portion or all of the processor 40 may be situated in the cartridge 14. Processor 40 in FIG. 17b may communicate externally from the cartridge 14 via line 155. The cartridge 14 in FIGS. 17a and 17b may have a set of valves that are closed to seal off the fluids in the reservoirs 64 and 66 while cartridge 14 is on the shelf. The valves may be mesovalves. Processor 40 may control valves via a line 113 and a connection block 111 providing a connection from the valves to line 113. Also, the input 32 may be closed off from blood reservoir 62 with a valve 109. Valve 109 may be a mesovalve or other microvalve connected to processor 40. While cartridge 14 is on the shelf, downstream valves between the flow sensors and mechanism 88 may be closed. Also, before cartridge 14 is used and until its system is pressurized, the downstream valves may be closed. The closure and open status of the downstream valves may be controlled by processor 40 via line 95 and connection block 110. Porous filters 61, 63 and 65 to reservoirs 62, 64 and 65, respectively, may prevent the passage of liquid but permit the passage of air, assuming the valves of block 111 are open, to enter the reservoirs 62, 64 and 66, so that when the liquids are pumped out the respective reservoirs, the removed liquids may be replaced by air so that a vacuum in not developed in the reservoirs.

A blood sample may be entered into the blood reservoir 62 via port 32. A pump 81 may pump blood from reservoir 62 through a flow sensor 80 into the flow mechanism 88. Flow sensor 80 provides a signal indicating a rate of flow of the blood via connection block 48 and line 93 to processor 40. Processor 40 may control the amount of flow through sensor 80 by a control signal to pump 81 via line 89 and connection block 87.

Lysing liquid in the lyse reservoir 64 may be pumped through flow sensor 100 by a pump 83. Flow sensor 100 may sent a signal to processor 40, indicating a rate of flow of the lyse through the sensor into the flow mechanism 88. This signal may go to processor 40 via the connection block 48 and line 93. Processor 40 may adjust the rate of flow of the lyse through sensor 100 with a signal sent to pump 83 via line 89 and connection block 87.

Sheath fluid may be pumped by pump 85 from the sheath reservoir 66 through a flow sensor 102 on into the flow mechanism 88. Flow sensor 102 may send a signal indicating the amount of flow of the sheath liquid passing through the sensor 102. This signal may go to processor 40 via the connection block 48 and line 93. Processor 40 may adjust the amount or rate of flow of the sheath liquid through sensor 102 and into mechanism 88 with a signal sent to pump 85 via the line 89 and connection block 87.

The sample blood may enter mechanism 88 and be lysed with the fluid pumped from reservoir 64 through sensor 100 to remove the red blood cells. The lysed blood may go through a flow channel (50) with a sheath liquid around the blood causing the white cells in the blood to go through the flow channel in single file. The white cells and other particles may be illuminated with light from the light sources. Light from the flow channel may be detected by detectors. The light sources may be controlled by processor 40 via line 97 to mechanism 88. The detectors may provide information signals to processor 40 via line 97. Flow mechanism 88 and the flow channel with its optics are described in other places of the present description. After the blood sample along with the sheath liquid leave the flow channel of the mechanism, it may go into the waste reservoir 52.

FIGS. 18a-18d show a microfluidic cartridge or chip 14 which may be produced with a rapid prototyping, laser-cutting lamination technology. A single type of reagent may be used, but for the convenience of driving, three reagent reservoirs may be included on the fluidic cartridge or chip 14, together with a waste container 52. Also, on the chip may be a sample-collecting capillary 32. The reagent reservoirs 62, 64 and 66 may have a pneumatic/hydraulic interface with the cover of the cytometer, which may ensure fluid driving inside of the fluidic chip 13. The interface may be either a flexible diaphragm or a porous plug (the latter is shown) 61, 63 and 65 that may permit air to move through, but prevent fluid loss. Plugs 61, 63 and 65 may be located at ports 123, 125 and 126, respectively. As part of a fluid-driving system, flow-sensor dies 80, 100 and 102 may be included on the fluidic chip. The electrical connection may be achieved through metal lines deposited on the cartridge 14 and connected to the external holder.

During storage, a removable cap 114 may be attached to the microfluidic circuit of chip 14. Lyse may be stored on board in reservoir 64. Valves 115 and 116 may be open. Valves 117, 118, 119 and 121 may be closed. One may do an analysis or test on cartridge 14.

Cap 114 may be removed and a drop of blood may put into the sample inlet 32. Capillary action may draw the blood into the sample storage sub-circuit. The cap 114 may be snapped on to the sample inlet 32 and the cartridge 14 may be placed into the cytometer case or bench apparatus.

Figure 18A:
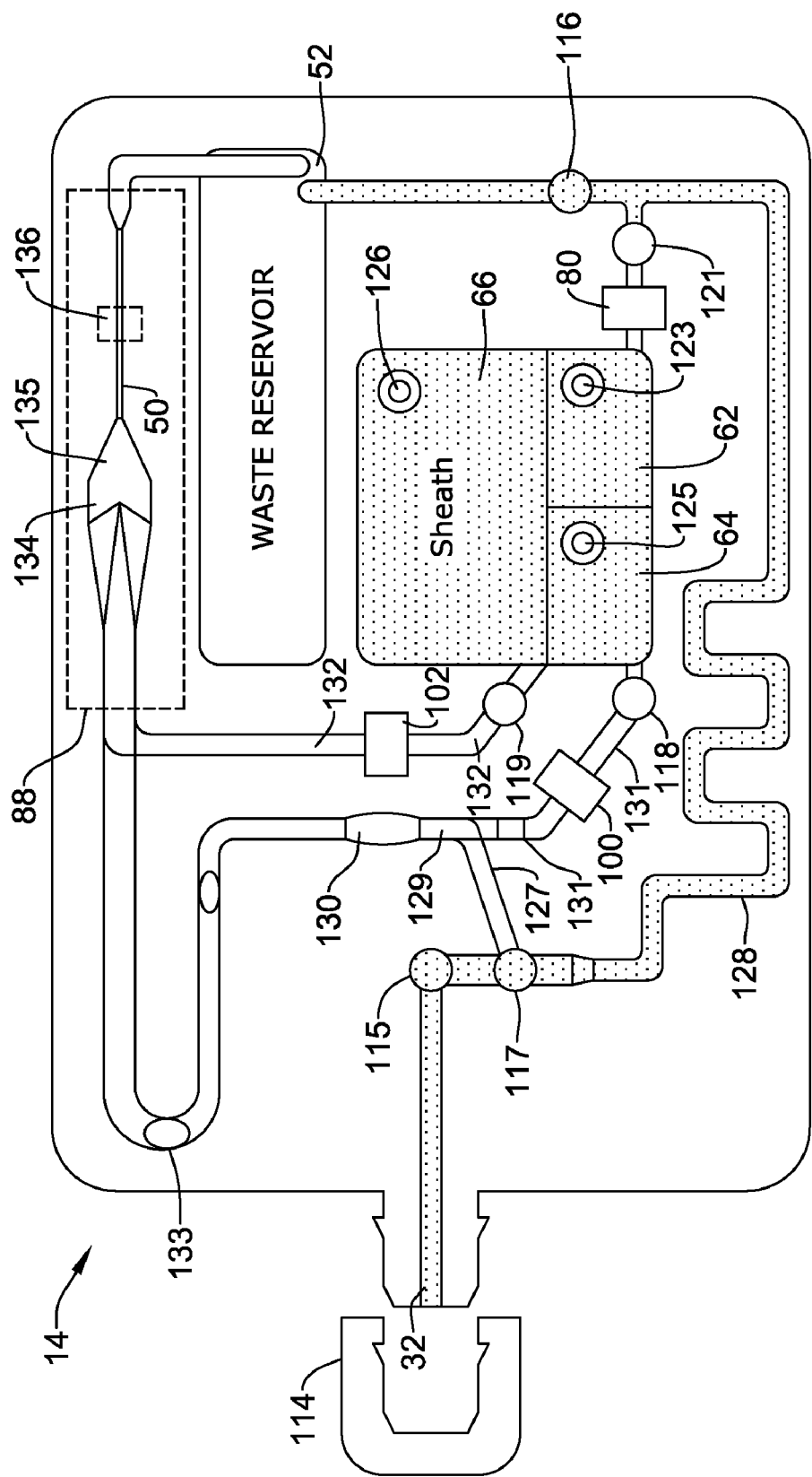
FIGS. 18a-18d show a various stages of fluid flow in a microfluidic circuit in cartridge or chip.
Figure 18B:
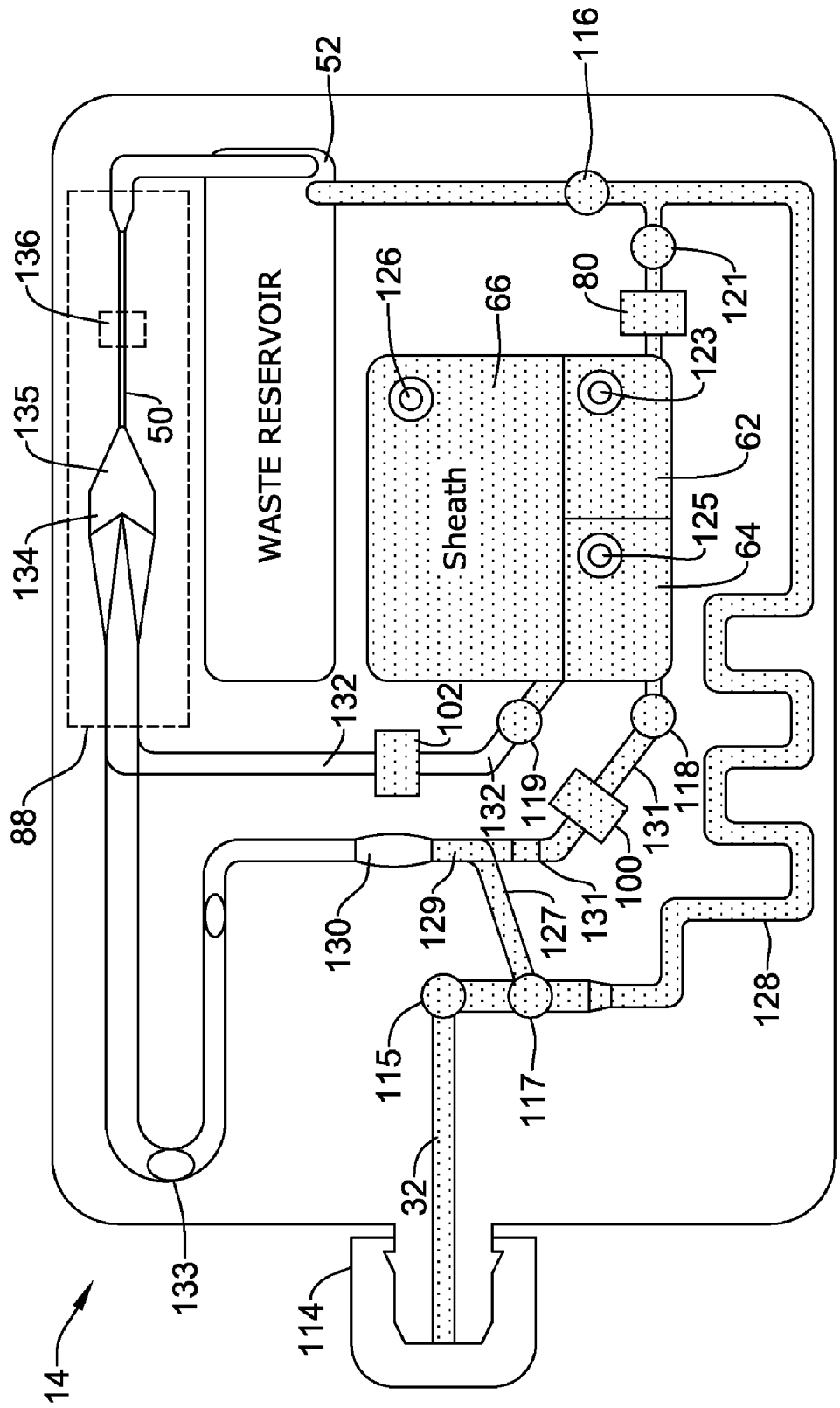
Figure 18C:
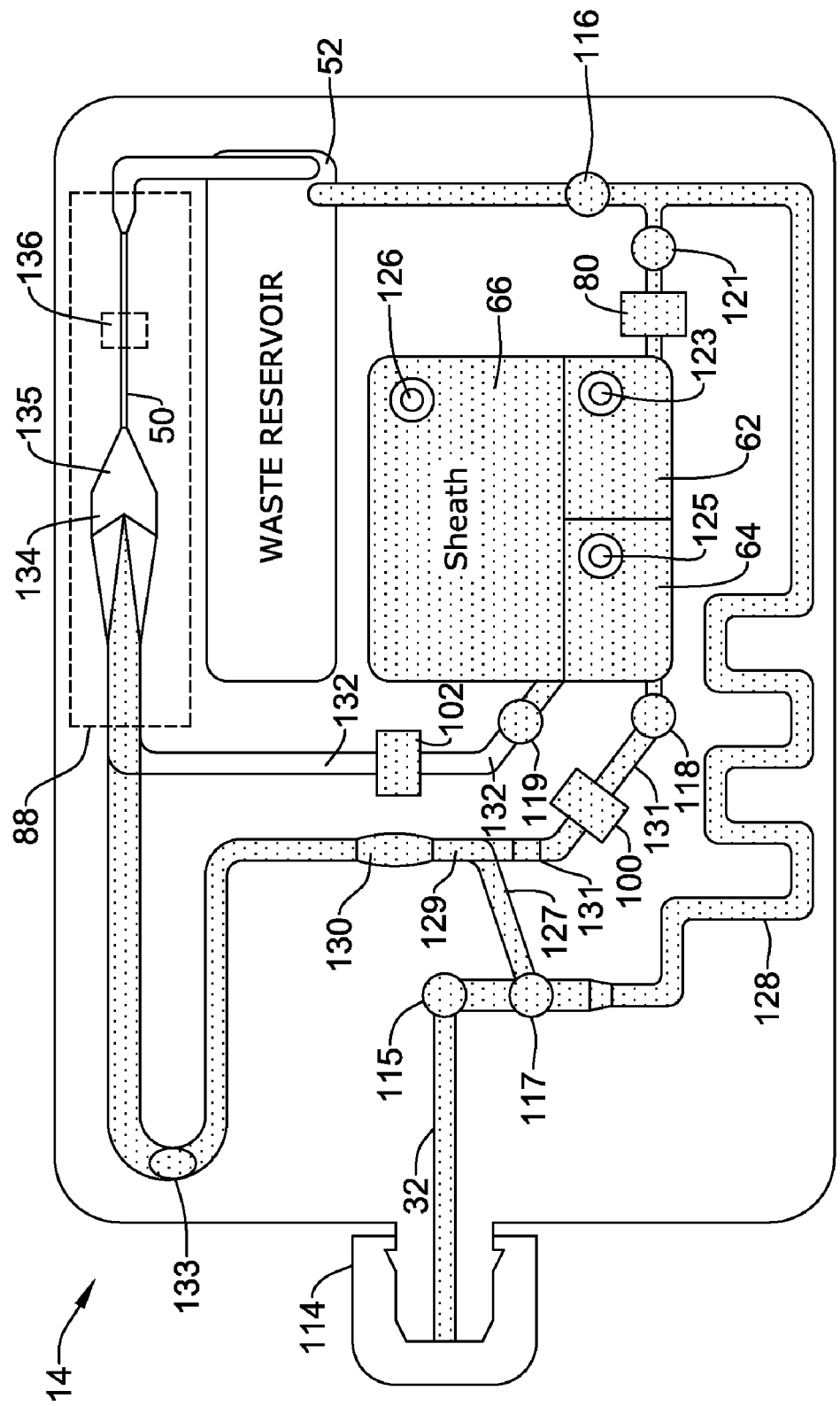
Figure 18D:
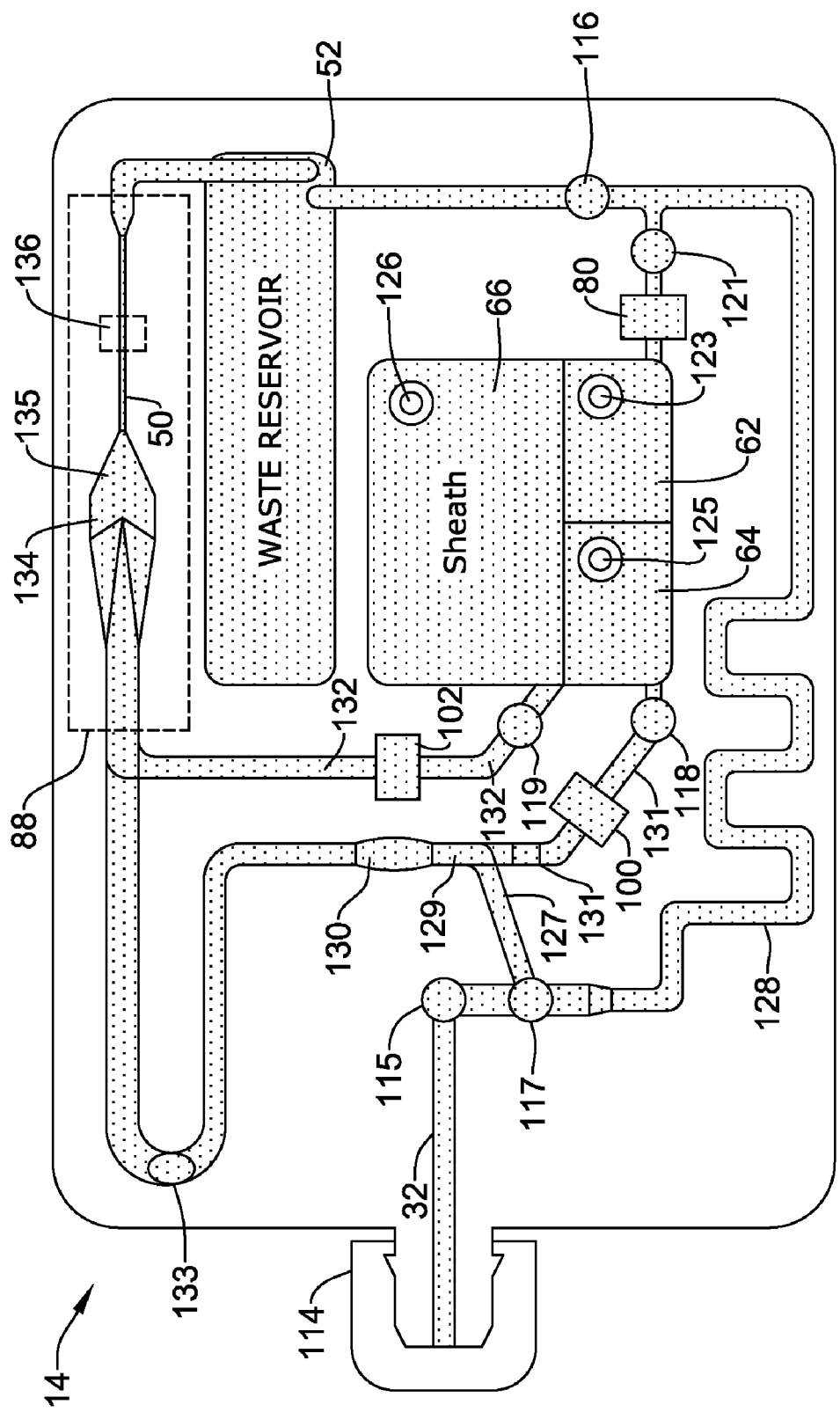

By closing the cover of the chip, card or cartridge 14 holder, valves 115 and 116 may close and valves 117, 118, 119 and 121 may open as in FIG. 18b. Reservoirs 62, 64 and 66 may be driven by different pressures at ports 123, 125 and 126, respectively, to produce different flow rates in the corresponding fluid lines. Whole blood may be pushed into the sample injector 129 by blood driver/reservoir 62 via valve 121, line 128, valve 117 and line 127 at a flow rate of approximately 0.1 microliter per second. In parallel, lyse from reservoir 64 may be pushed, via valve 118 and line 131 of FIG. 18b, on to sample injector 129 at a flow rate of approximately 1 microliter per second. In FIG. 18c, the lyse and whole blood may be co-eluded into a mixing and lysing channel 133 to produce a total of about 13 microliters of about 10 to 1 diluted blood (viz., the sample). The red blood cells are lysed, leaving white blood cells remaining in the sample. In FIG. 18d, a sheath fluid may be pushed via valve 119 and line 132 into a focusing chamber 134 at a rate of about 7 microliters per second. Blood flow may be stopped with the reduction of the pressure load in reservoir 62 to zero, while the pressure load in reservoir 64 is adjusted to produce a sample (lysed blood) at a flow rate of about 0.5 microliter per second. The sheath fluid in chamber 134 may cause the while cells of the blood sample to be hydrodynamically focused or the like in area 135 into single file core stream to flow through flow channel 50. These flow rates may be needed for producing a core stream with dimensions of about 10×5 microns in the cytometer flow channel 50.

The particles or cells in flow channel 50 may pass by the light source and detector system 136. Small angle scattering (SALS), forward angle scattering (FALS) and large angle scattering (LALS) caused by the particles in the flow stream may be detected. Arrays of light sources and detectors may be used. Also, interruptions of direct light may be detected. Particle width, length, center and velocity may be determined. Various other properties and identification information of the particles may be obtained with the optical system.

A previous cytometer system used so-called volume-controlled flow, generated by miniature syringe pumps driven with stepper motors or manually, to drive all reagents and the sample through the microfluidic circuit of cartridge 14. The system may be precise but is extremely bulky and uses significant electrical power. In order to miniaturize and make energy efficient the fluid driving system, the open-loop, very precise and stable but bulky and expensive fluid driving elements may be replaced with less precise and less stable pressure sources which can be adjusted in a closed loop configuration to maintain a constant, desired flow velocity at critical points of the fluidic circuit. Implementation of this approach may rely on small and sensitive fluid flow sensors for measurement of flow rates as low as 10 nanoliters per second in sub-millimeter channels, and fast and small actuators for closed loop, pressure control.

There may be a manually pressurized system described in other places of this description. Another approach may involve active pumping accomplished with mesopump channels. FIGS. 19a and 19b reveal an application of the mesopumps 137 and mesovalves 138 embedded in a chip, card or cartridge 14. There may also be embedded flow sensors 139 in chip 14. FIGS. 19a and 19b show an illustrative example of a portion of a fabricated chip or cartridge 14 with the embedded components. FIG. 19b is a top view of the portion of a cytometer and FIG. 19a is a cut away side view revealing the structural relationship of the components relative to the chip 14. Configurations of the cartridges as shown in FIGS. 16, 17a and 17b, as illustrative examples, may have embedded mesopumps 137 as pumps 81, 83 and 85, and mesovalves 138 as the valves in blocks 110 and 111 of FIGS. 16, 17a and 17b, and mesovalves 138 as valves 74, 76, 84, 86, 94 and 96 of pressure chambers 72, 75 and 77 of FIG. 16. Other valves in the system may be embedded mesovalves 138. Similarly, valves 115-119 and 121 of the cartridge 14 of FIGS. 18a-18d may be embedded mesovalves 138. Flow sensors 80, 100 and 102 of cartridge 14 of FIGS. 16, 17a, 17b, 18a-18d, 19a and 19b may be embedded flow sensors 139. However, the pumps and valves may be another kind of small valves and pumps.

Mesopumps 137 may be, for an example, dual diaphragm pumps which are in principle described in U.S. Pat. No. 6,179,586 B1, issued Jan. 30, 2001, which is incorporated herein by reference. Also, information related to mesopumps and valves may be disclosed in U.S. Pat. No. 5,836,750, issued Nov. 17, 1998, which is incorporated herein by reference. U.S. Pat. Nos. 6,179,586 B1 and 5,836,750 are owned by the entity that owns the present invention.

Figure 20A:
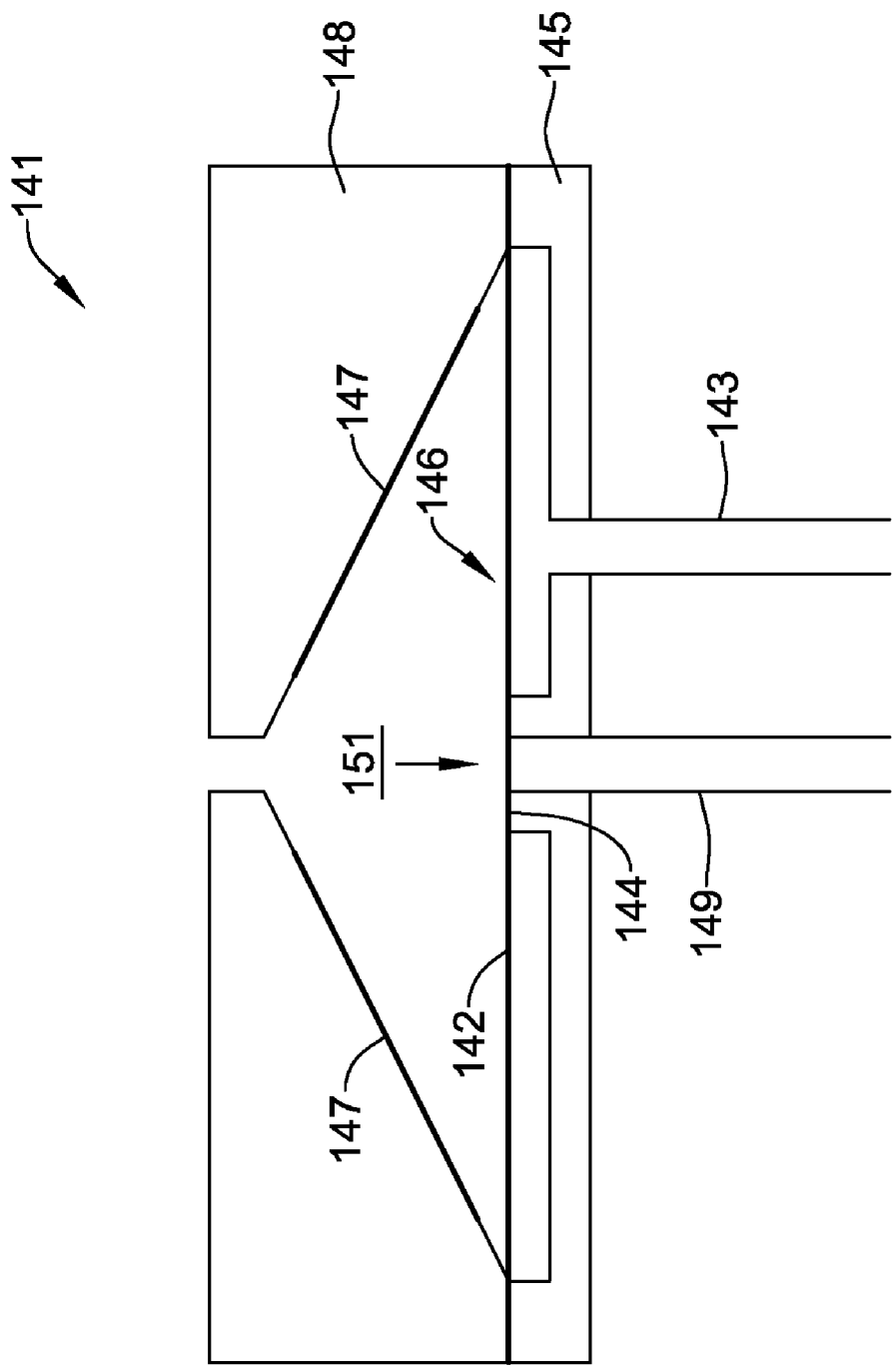
FIGS. 20a and 20b reveal an illustrative example of a mesovalve in a closed state and an open state, respectively.
Figure 20B:
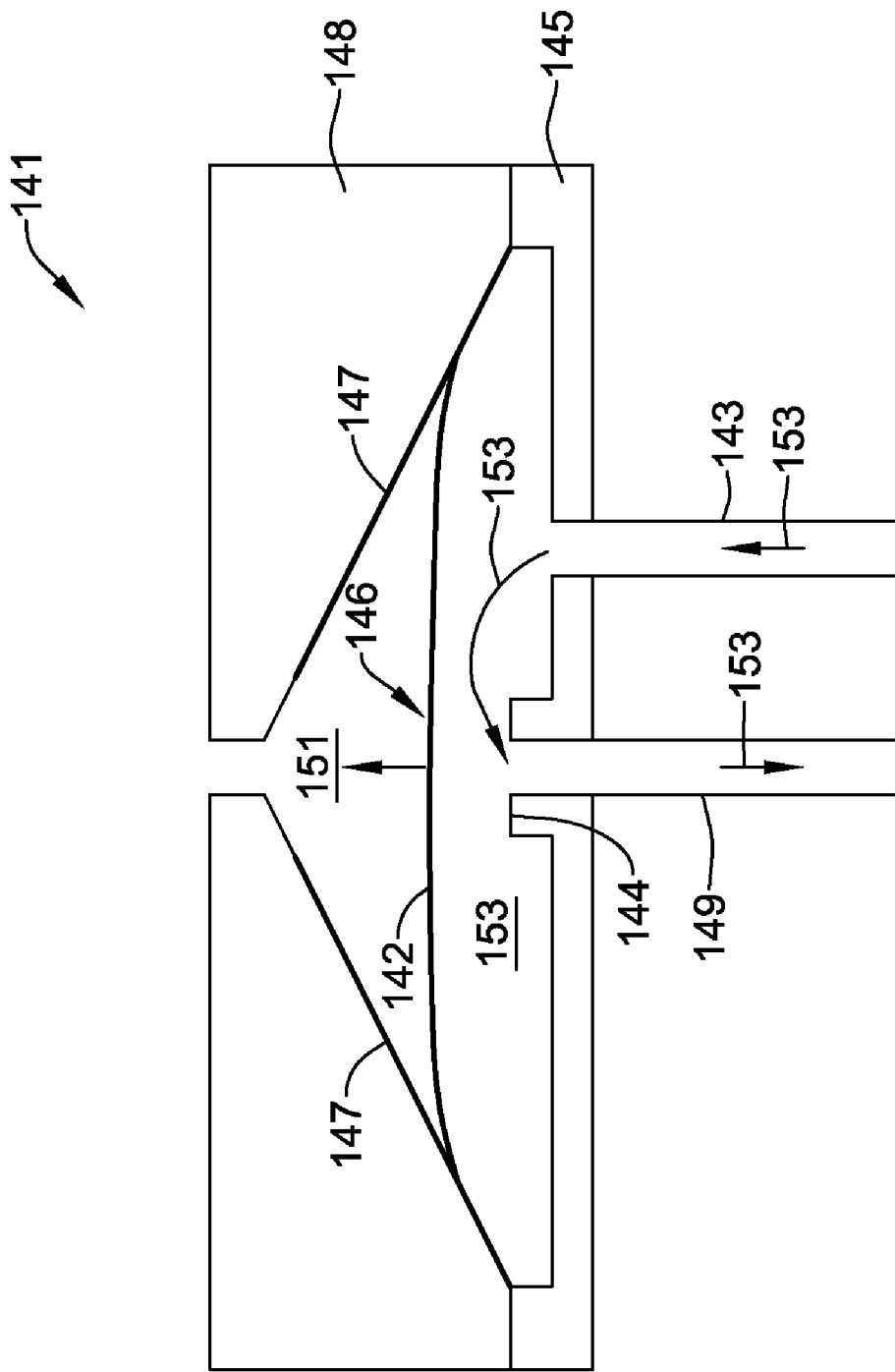

FIGS. 20a and 20b reveal an illustrative example of a mesovalve 141 in a closed state and an open state, respectively. In FIG. 20a, there may be a diaphragm 142 closing off an output port 149 at the valve-like seat 144 of a lower structure 145. Diaphragm 142 may have a first electrode 146 coated on it. Surfaces of an inside cavity 151 of a top structure 148 may have a second electrode 147 coated on them. Lower structure 145 may have an input port 143 to the mesovalve 141. Diaphragm 142 may seal the output port 149 from the tension of diaphragm 142 being held between the upper and lower structures. The valve seat 144 upper surface may be slightly higher than the surface of the perimeter of the lower structure 145 securing the diaphragm 142. Also, there may be a repelling electrostatic force between electrodes 146 and 147 pushing diaphragm 102 against the valve-like seat 144.

In FIG. 20b, diaphragm 142 may be lifted off of valve-like seat 144 with an attracting electrostatic force between the electrode 146 attached to diaphragm 142 and electrode 147 adhered to the inside surfaces of top structure 148. With diaphragm 142 lifted off of surface or seat 144, a fluid 153 may flow from the import port 143 in a cavity 153 below diaphragm 142, through the cavity, and past the seat surface 144 into the output port 149. The electrostatic force attracting electrodes 146 and 147 may be caused by an application of an electrical voltage to the electrodes 146 and 147. When the electrical voltage across the electrodes 146 and 147 is removed, electrostatic attraction between diaphragm 142 and the inside surfaces of top structure 143 disappear, diaphragm 142 may fall and return its original position against surface 144 which seals off the output port 149 to stop the flow of fluid 153 through the mesovalve 141.

Figure 22:
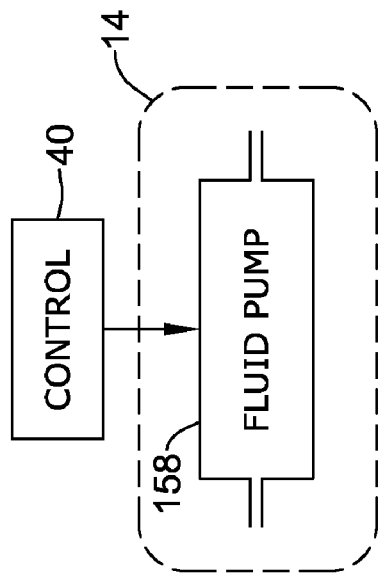
FIG. 22 is a diagram of a fluid pump on a cartridge with open loop control.
Figure 21:
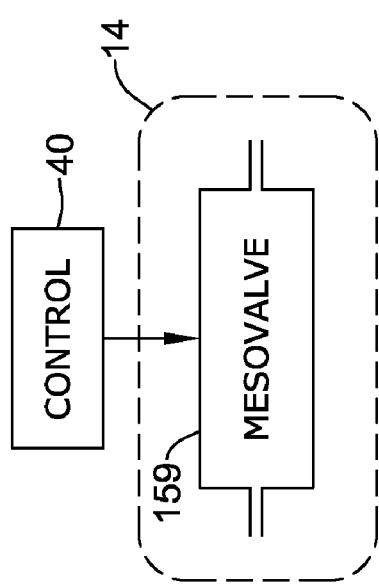
FIG. 21 is a diagram of a the cartridge having a mesovalve with open loop control.

FIG. 21 shows a fluid micro or mesovalve 159 situated or embedded in the cartridge 14, having an off-cartridge controller 40 connected to the valve. Valve 159 may be another kind of valve situated in the cartridge. FIG. 22 shows the cartridge 14 having a fluid pump 158 embedded or built into it. Pump 158 may provide unidirectional or bidirectional flow. The pump may be a mesopump or other kind of a pump. It may be utilized for gas or liquid. Pump 158 may be open-loop controlled by control 40. Control 40 may be a processor and/or a controller. The present pumps and valves discussed in this description may have thicknesses from 0.8 mm to 1.0 mm, which might be reduced. However, the pumps and valves may be as thin as 0.2 mm. Application of various technologies may reduce the thicknesses even further. The pumps and valves may have diameters of about 10 mm. The pumps and valves may be stacked upon each other whether they are connected to one another or not. The range of thicknesses of cartridge 14 may be about 1 mm to 5 mm, i.e., generally a thickness less than 6 mm, but should be less than 10 mm, although it could be thinner than 1 mm. Lateral dimensions of the cartridge 14 may be less than 5 cm by 7 cm, but should be less than 10 cm by 15 cm, or an area less than 150 square cm. The cartridge could be about the size of a typical credit card. In certain applications, the cartridge may be thicker than 10 mm and/or larger than 10 cm by cm or an area larger than 150 square cm. This larger size cartridge may encompass much more complex microfluidics. The pumps and valves may be encompassed in the cartridge 14 using laminate technologies. There may be embedded components such as pumps and valves that are put into the cartridge or built in as a part of the layers of the cartridge. The cartridge 14 may also have other components including flow sensors, pressure sensors, passage ways, devices for preventing a flow of liquid, channels and reservoirs for fluids and their flow. These components may be micro-components, including mesopumps and mesovalves. The pumps may be unidirectional or bidirectional. Some of these components may be situated on the cartridge and some may be situated off the cartridge 14. The combination of on-cartridge and off-cartridge components may vary according to application of the cartridge. Not all combinations of on-cartridge and off-cartridge components are necessarily shown in the Figures of the present description. The cartridge 14 may be treated as a disposable or non-disposable item after usage. When used for blood analysis, the cartridge 14 would likely be disposed of for sanitary reasons. If the cartridge is used for water, environmental, pollutant or like analysis, the cartridge 14 may be reusable.

Figure 24:
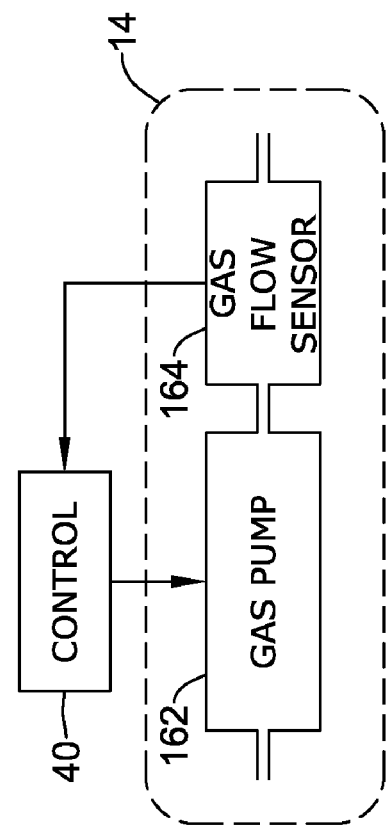
FIG. 24 shows a gas pump and flow sensor on a cartridge, with closed loop control.
Figure 23:
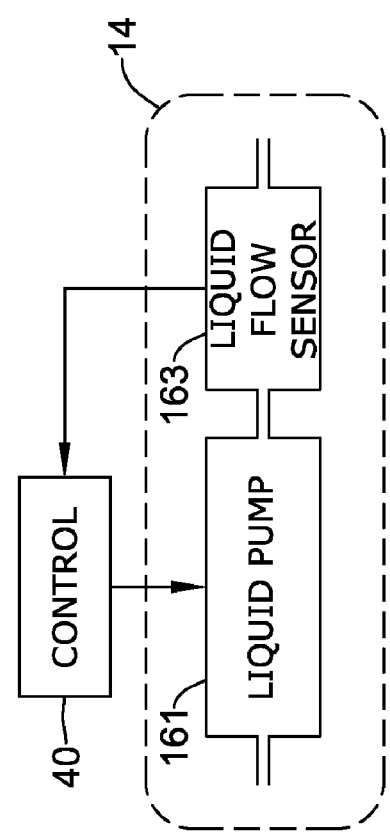
FIG. 23 shows a liquid pump and flow sensor on a cartridge, with closed loop control.

The flow of fluid in the configuration of FIG. 22 may be determined by noting the number of cycles of pump 158 per volume unit of flow. The flow amount may be set by control 40 of the pump. FIG. 23 shows a liquid pump 161 on the cartridge 14. Pump 161 may be unidirectional or bidirectional. A liquid may be pumped by pump 161 in either direction past a liquid flow sensor 163. The sensor 163 may also be embedded or built into cartridge 14. Flow sensor 163 may provide a feedback signal to control 40 to indicate the amount and direction of flow. Control 40 may maintain a closed loop control of pump 161 so as to provide a specific flow on cartridge 14. FIG. 24 shows a similar type of fluid circuit as that in FIG. 23, except it shows a gas pump which may be designed to pump a gas in one or two directions in cartridge 14. The pumps in the various configurations of this description may be a mesopumps or other kinds of micropumps. Also, the valves of the configurations may be mesovalves or other kinds of microvalves. Some of these pumps may pump both gas and liquid. A gas flow sensor 164 may indicate a direction and an amount of flow on cartridge 14. A gas flow indication may be sent to control 40 which in turn provides an input to pump 162 so as to provide a desired flow.

Figure 25:
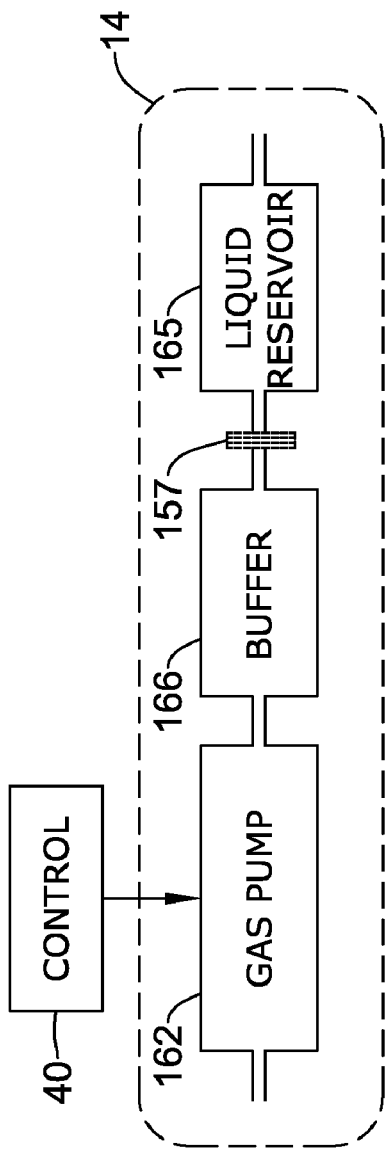
FIG. 25 shows a gas pump, buffer and liquid reservoir on a cartridge, with open loop control.
Figure 26:
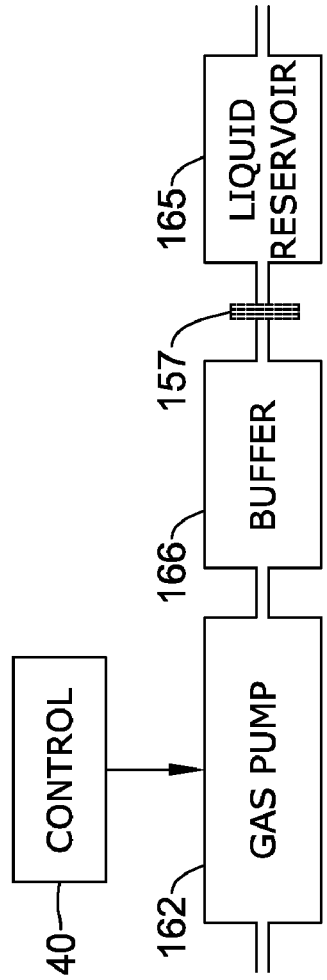
FIG. 26 is similar to FIG. 25, except the components are off the cartridge.

FIG. 25 shows another pumping configuration for providing or removing a liquid from a reservoir 165 on a cartridge 14. The pump 162, open loop controlled by control 40, may provide gas through a buffer 166 (which may be like a pressure chamber) to apply pressure to the reservoir 165. Buffer 166 may smooth out the pulsations in the gas flow caused by gas pump 162. There may be a device or membrane 157 that may permit gas but not liquid to go through it. The buffer 166 may not be needed in some configurations. The gas may go to a liquid reservoir 165 and with a build up of pressure of the gas on the liquid in the reservoir 165 to push out the liquid from the reservoir. FIG. 26 shows a similar configuration not on a cartridge 14. Certain portions of this configuration may be on or off of the cartridge 14.

Figure 27:
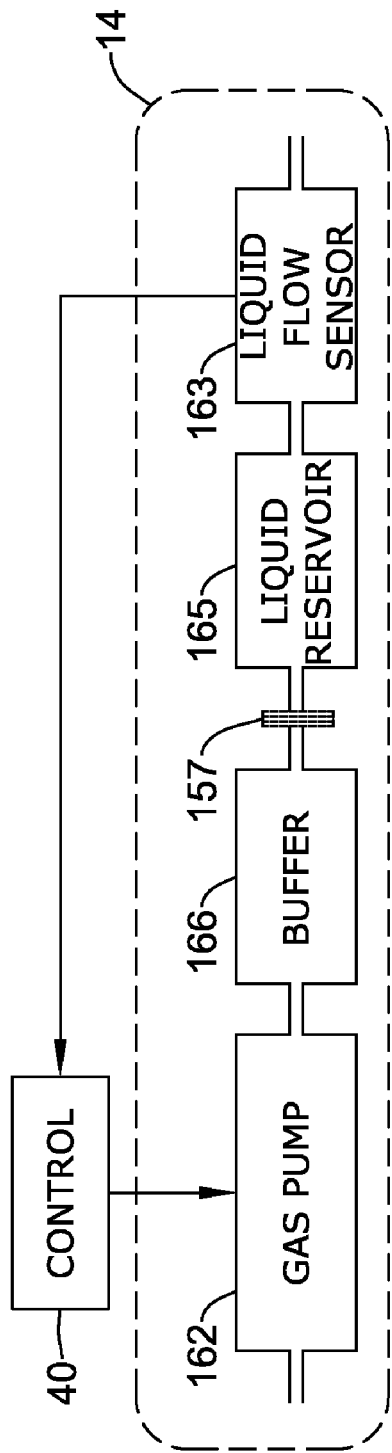
FIG. 27 is similar to FIG. 25, except it also includes a flow sensor and closed loop control.
Figure 28:
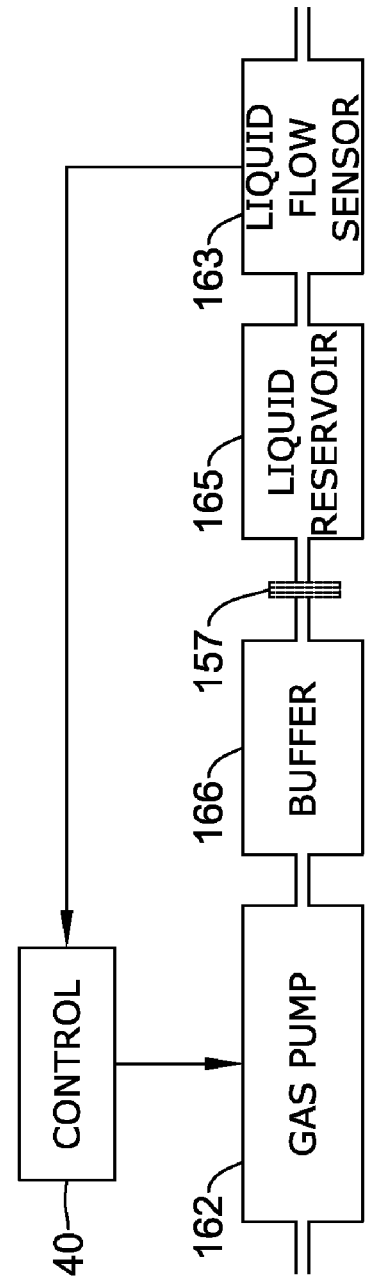
FIG. 28 is similar to FIG. 27, except the components are off the cartridge.

FIG. 27 is similar to FIG. 25 except that the configuration of the FIG. 27 has a closed loop control with a flow sensor 163. The gas pump 162 may pump a gas to liquid reservoir 165 via buffer 166. Pump 162 may be unidirectional or bidirectional. Gas to the reservoir 165 may provide pressure on the fluid to move it from the reservoir 165 through the liquid flow sensor 163. A device 157 may prevent liquid from flowing back into buffer 166 but will let gas go through in either direction. The flow sensor 163 may send a signal to control 40 indicating an amount of liquid flow from the reservoir. Control 40 may provide a signal to gas pump 162 to control the amount of gas pumped so as to maintain an appropriate gas pressure and/or desired flow of liquid from the reservoir 163, via the closed loop connections to and from control 40. FIG. 28 reveals a similar configuration of the one in FIG. 27, except that it may be wholly or partially off of the cartridge 14.

FIG. 29 reveals another configuration that may be inserted in cartridge 14. A gas 162 pump may pump a gas through a buffer 166 and onto a pressure chamber 167 at an input having a valve 168. Also, chamber 167 may have a relief-like valve 169. Valves 168 and 169 may be actuated by control 40 to open or close individually. The pump 162 may be unidirectional or bidirectional. The gas may proceed from chamber 167 to the liquid reservoir 165 where a pressure of the gas on the liquid in reservoir may force the liquid through the liquid flow sensor 163. Flow sensor 163 may be off of the cartridge 14 but still coupled to the microfluidic circuit on the cartridge. Flow sensor 163 may send a signal indicating flow to control 40. Control 40 may assure that pump 162 is pumping sufficient gas. However, the amount of liquid flow through flow sensor 163 may be controlled by an amount of pressure in chamber 167. If more pressure is needed for increased flow through sensor 163, control 40 may open valve 168 and close valve 169. If the pressure needs to be decreased to reduce liquid flow through sensor 163, then control 40 may close valve 168 and open valve 169. Valves 168 and 169 may be mesovalves embedded or built into the cartridge 14. The closed loop control may be limited to just the flow sensor and valve operation. Pump 162, in either configuration, may be a mesopump or other micropump. FIG. 30 shows another configuration on cartridge 14 having some resemblance to the configuration of FIG. 29; however, the flow sensor 163 may be on the cartridge 14.

Figure 31:
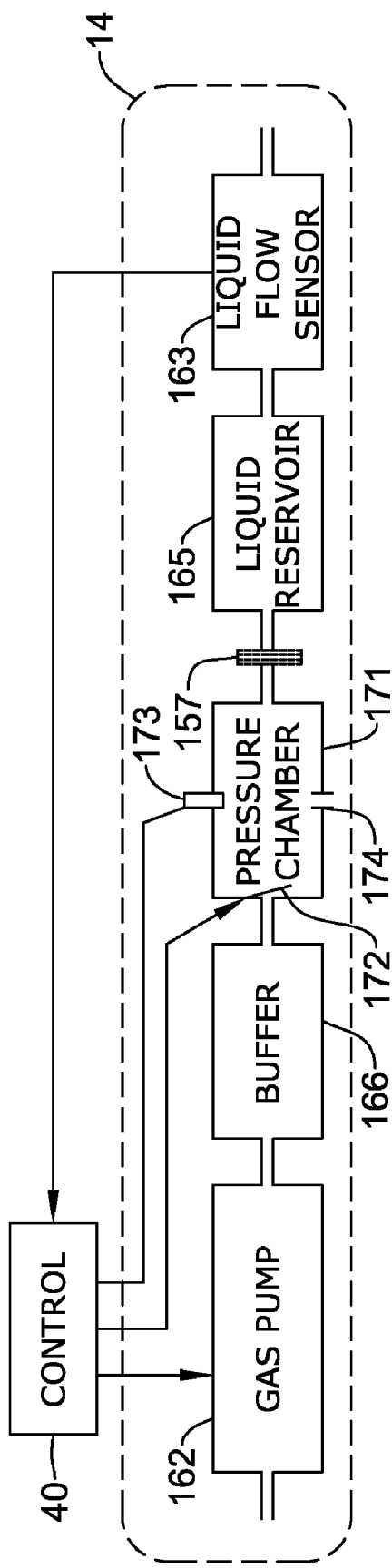
FIG. 31 is similar to FIG. 30, except the pressure chamber has a different configuration.
Figure 32:
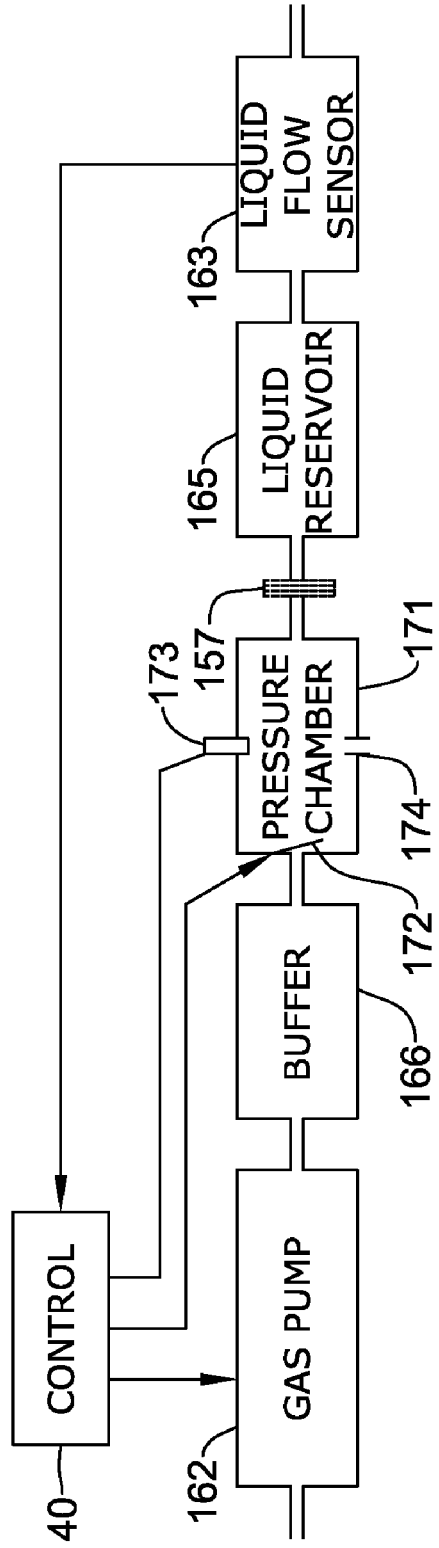
FIG. 32 is similar to FIG. 31, except the components are shown as off the cartridge.

FIG. 31 shows a configuration having a pressure chamber 176 being controlled differently than chamber 167 of FIGS. 29 and 30. A gas pump 162 may pump gas through a buffer 166 on to a pressure chamber 171 via a valve 172. The gas under pressure may go to liquid reservoir 165. The gas on the liquid in the reservoir may force the liquid out of the reservoir on through the flow sensor 163. A signal indicating liquid flow may be sent from sensor 163 to control 40. Control 40 may assure that pump 162 is pumping a sufficient amount of gas. However, the amount of liquid flow through flow sensor may be controlled by an amount of pressure on the gas in chamber 167. The amount of pressure may be detected by pressure sensor 173 in chamber 171, and a signal indicating the amount of pressure may be sent from sensor 173 to control 40. If more flow of liquid is to go through flow sensor 163, then valve 172 may be at least partially opened; and if less flow of liquid is to go through the flow sensor, then valve 172 may be moved to a more closed position but not necessarily be completely closed. The opening and closure of valve 172 may be controlled by signals from control 40. Instead of a relief valve 169 as in FIG. 31, a restrictor 174 may be placed in the pressure chamber 171 to provide some leakage or relief of gas from chamber 171. Valve 172 may be a mesovalve embedded or built into the cartridge 14. Similarly, the restrictor or orifice 174 may be built into cartridge 14. Pressure sensor 173 may be embedded of built into cartridge 14. FIG. 32 may have a similar configuration as that of FIG. 31, except that the configuration of FIG. 32 is shown as off of the cartridge. Also, FIG. 33 may have a similar configuration as that of FIG. 30, except that the latter is shown as off of the cartridge. Certain portions of either configuration may be on or off the cartridge.

The configurations of FIGS. 29-33 may have several closed loop control arrangements which may be implemented separately or in combination. The flow sensor and gas pump in conjunction with each other may provide sufficient closed loop control. The pressure chamber and its valves with a flow sensor may provide sufficient closed loop control. In FIGS. 31 and 32, the pressure chamber with the pressure sensor and valve may separately provide sufficient closed loop control.

Although the some of the components discussed in FIGS. 21-33, except control 40, may reside on the cartridge 14, some of the components may be located off of the cartridge. Further, control 40 may be a chip embedded or built into the cartridge 14, although control 40 or a portion of it may often be located off of the cartridge. In FIGS. 27 and 29-31, gas pump 162 and/or buffer 166 may be located off the cartridge 14. They may be connected via ports and tubing or other plumbing to cartridge 14 when the cartridge is placed into a holder that facilitates the fluid and electrical connections and optical interface for cartridge 14. The cartridges 14, as in FIGS. 21-25, 27 and 29-31, may be shown merely in part. These cartridges may have additional components relevant to specific applications.

Liquid flow sensor 163 may be embedded or built into the cartridge 14 or it may be removed from the cartridge which may be disposed of after usage, and reused in another cartridge 14. Liquid flow sensor 163 may be may be removable from a slot or holder in one cartridge 14 for reusability in another cartridge with a similar slot or holder. The same may apply to the gas flow sensor 164. The various off-cartridge components may be connected to the components on the cartridge 14 via appropriate plumbing.

Even though the FIGS. 21-33 show one channel for cartridge 14, a cartridge 14 may have two or more channels having similar or differing configurations. Also, cartridge 14 may have a flow channel or like mechanism associated with the configurations of FIGS. 21-33. A flow channel and additional components may be on the cartridge 14 even for configurations in the Figures revealing some or all of the components shown in the respective Figures as being off the cartridge.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A flow control system comprising:

a fluidic cartridge having at least one flow channel;

an electrostatically actuated valve situated in at least one flow channel of the cartridge, wherein the electrostatically actuated valve includes a valve cavity with a movable diaphragm within the valve cavity, wherein the movable diaphragm is actuated by an electrostatic force to open the electrostatically actuated valve to allow flow through the at least one flow channel and/or close the electrostatically actuated valve to prevent flow through the at least one flow channel;

a controller connected to the electrostatically actuated valve for controlling the opening and/or closing of the electrostatically actuated valve during operation of the fluidic cartridge; and a flow sensor in fluid communication with the at least one flow channel, the flow sensor measuring the velocity of fluid flow, and the controller controlling the valve to achieve a desired fluid velocity in the at least one flow channel.

2. The system of claim 1, wherein the electrostatically actuated valve is a mesovalve.

3. A flow control system comprising:
a fluidic cartridge having at least one flow channel;
a pump situated in the cartridge, the pump in fluid communication with at least one flow channel of the cartridge;
a controller connected to the pump; and
a flow sensor situated in the cartridge and in fluid communication with the at least one flow channel of the cartridge, the flow sensor providing a flow signal representing the fluid velocity to the controller, and the controller controlling the pump to achieve a desired flow profile in the at least one flow channel of the cartridge.

4. The system of claim 3, wherein the pump is a bidirectional pump.

5. The system of claim 3, wherein:
the pump is a liquid pump; and
the flow sensor is a liquid flow sensor.

6. The system of claim 3, wherein the pump is gas pump.

7. The system of claim 6, wherein the pump is an electrostatically actuated gas pump.

8. The system of claim 7, further comprising a reservoir fluidly connected to gas pump.

9. The system of claim 8, wherein the flow sensor is fluidly connected to the reservoir and electrically connected to the controller.

10. The system of claim 3, further comprising:
a buffer fluidly connected to the pump; and
a reservoir fluidly connected to the buffer.

11. The system of claim 10, wherein the flow sensor is fluidly connected to the reservoir.

12. The system of claim 11, wherein:
the pump is a gas pump; and
the reservoir is a liquid reservoir.

13. The system of claim 3, further comprising:
a pressure chamber fluidly connected to the pump; and
a reservoir fluidly connected to the pressure chamber.

14. The system of claim 13, wherein the pressure chamber comprises:
an inlet valve connected to the controller; and
a relief valve.

15. The system of claim 14, wherein:
the pump is an electrostatically actuated pump; and
the valves are electrostatically actuated valves.

16. The system of claim 14, wherein the flow sensor is fluidly connected to the reservoir and electrically connected to the controller.

17. The system of claim 3, further comprising:
a pressure chamber fluidly connected to the pump; and
a liquid reservoir fluidly connected to the pressure chamber.

18. The system of claim 17, wherein the fluidic cartridge has a thickness of less than 10 mm and an area less than 150 cm2.

19. The system of claim 17, wherein the pressure chamber comprises:
an inlet valve connected to the controller; and
a pressure sensor connected to the controller.

20. The system of claim 19, wherein the flow sensor is fluidly connected to the reservoir and electrically connected to the controller.

21. The system of claim 20, further comprising a buffer fluidly connected between the pump and the pressure chamber.

22. The system of claim 21, wherein:
the pump is a gas pump; and
the reservoir is a liquid reservoir.

23. The system of claim 22, wherein:
the pump is an electrostatically actuated pump; and
the valve is an electrostatically actuated valve.

24. The system of claim 20, wherein the flow sensor is situated off of the cartridge.

* * * * *